United States Patent [19]

O-Yang et al.

[11] Patent Number: 5,192,749

[45] Date of Patent: Mar. 9, 1993

[54] 4'-SUBSTITUTED NUCLEOSIDES

[75] Inventors: Counde O-Yang, Sunnyvale; Keith A. M. Walker, Los Altos Hills; Walter Kurz, Mountain View; Helen Y. Wu, San Jose, all of Calif.

[73] Assignee: Syntex (U.S.A.) Inc., Palo Alto, Calif.

[21] Appl. No.: 526,485

[22] Filed: May 21, 1990

[51] Int. Cl.⁵ .................. A61K 31/70; C07H 17/00; C07H 15/12

[52] U.S. Cl. .................. 514/45; 514/46; 514/47; 514/48; 514/49; 514/50; 514/51; 514/934; 536/26.12; 536/26.13; 536/26.14; 536/26.26; 536/26.21

[58] Field of Search ................ 514/45-51, 514/934; 536/23, 24, 28

[56] References Cited

U.S. PATENT DOCUMENTS

| 3,817,978 | 6/1974 | Jenkins et al. | 260/210 R |
| 3,910,885 | 10/1975 | Moffatt et al. | 260/211.5 R |
| 3,928,319 | 12/1975 | Jenkins et al. | 260/211.5 R |

FOREIGN PATENT DOCUMENTS 0217580 of 1986 European Pat. Off.
WO87/01283 of 1987 PCT Int'l Appl.

OTHER PUBLICATIONS

"Synthesis of Certain 4'-Substituted Nucleosides", Verheyden et al., Ann. N.Y. Acad. Sci. 255, 151 (1975).

"4'-Substituted Nucleosides. 1. Synthesis of 4'-Methoxyuridine and Related Compounds", Verheyden et al., Journal of the American Chemical Society, 97(15), 4386 (1975).

"4-Substituted Nucleosides. 2. Synthesis of the Nucleoside Antibiotic Nucleocidin", Jenkins et al., Journal of the American Chemical Society, 98:11, 3346, (1975).

"Sythesis of 4'-Methoxyadenosine and Related Compounds", Verheyden et al., Carbohydrate Research, 100, 312 (1982).

"Nucleoside 4',5'-Enol Acetates. Synthesis and Chemistry of a Unique Uridine O²,4'-Anhydronucleoside", Cook et al., Journal of the American Chemical Society, 101(6), 1554 (1979).

Primary Examiner—John W. Rollins
Attorney, Agent, or Firm—James J. Wong; David A. Lowin

[57] ABSTRACT

Nucleosides compounds of Formula I:

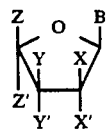

wherein
B is a purine or a pyrimidine;
X and X' are H;
Y is H;
Y' is OH, F or H;
or Y' and X' together makes a bond;
Z is

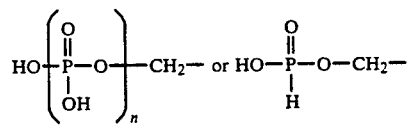

where n is zero, one, two or three; or Y' and Z together form a cyclic phosphate ester; Z' is —CN, —CH₃, CH₂N₃ or —CH₂J,
where J is a halogen atom;
or Z' and Y' together are —CH₂O—; and pharmaceutically acceptable esters, ethers, amides, N-acyl moieties and salts thereof.

31 Claims, No Drawings

4'-SUBSTITUTED NUCLEOSIDES

BACKGROUND OF THE INVENTION

1. Field of the Invention

The present invention relates to antiviral agents, particularly to nucleoside-based antiviral drugs, and specifically to a series of 4'-substituted nucleosides. The invention is also directed to formulations and methods for treating viral infections in a mammal, as well as to methods of making the subject compounds.

BACKGROUND INFORMATION

Viruses have long been known to be the cause of some of the most costly, troublesome and devastating infections to man. In recent years, this pattern has been underscored by the onset of Acquired Immune Deficiency Syndrome (AIDS), which has been found to be the result of infection by the human immunodeficiency viruses (HIV).

Various active agents have been proposed for the treatment of viruses such as those responsible for AIDS. Typically, these active agents have suffered from a disadvantageous therapeutic index, i.e., the ratio of activity to toxicity (in other words, their beneficial effect was outweighted by their toxic nature).

For example, the drug AZT (3'-azidothymidine) is described in European Patent Application 86307071.0; it is presently used for treatment of AIDS. It is not, however, a cure for the disease. AZT is also fairly toxic to the bone marrow, requiring patients under treatment to receive frequent blood transfusions, and although their disease symptoms are diminished and life is prolonged, AIDS related death is still considered inevitable.

Another example is the drug ddC (2',3'-dideoxycytidine), as described in PCT/US86/01626, having an international filing date of Aug. 8, 1986, claiming priority from U.S. patent application Ser. No. 769,017, filed Aug. 26, 1985. This drug is currently under investigation for the treatment of HIV infection. It is more potent than AZT, but, it is also very toxic, leading often to severe peripheral neuropathy.

4'-Substituted nucleosides have been described previously [see *Ann. N.Y. Acad. Sci.*, 255, 151 (1975)]. More particularly, various 4'-methoxypurine and 4'-methoxypyrimidine ribonucleosides and 4'-azidocytidine have been synthesized and screened for their antiviral activity, but, have not shown any usefulness in this regard. For example, 4'-azidocytidine is cytotoxic and devoid of anti-HIV activity.

5-Chloro-substituted derivatives of 2',3'-didehydro-2',3'-dideoxyuridine, 3'-fluoro-2',3'-dideoxyuridine and 3'-azido-2',3'-dideoxyuridine have been described previously [see Biochemical Pharmacology, Vol 38, No. 6, pp 869-74 (1989)]. Preliminary results there report that 5-chloro-substituted-3'-fluoro-2',3'-dideoxyuridine and 5-chloro-substituted-3'-azido-2',3'-dideoxyuridine exhibit potent antiviral activity. However, further studies are required to assess their therapeutic potential.

SUMMARY OF THE INVENTION

One aspect of the present invention relates to 4'-substituted nucleosides, i.e., the compounds of Formula I:

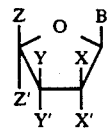

wherein:
B is a purine or a pyrimidine;
X and X' are H;
Y is H;
Y' is OH, F or H;
or Y' and X' together makes a bond;
Z is

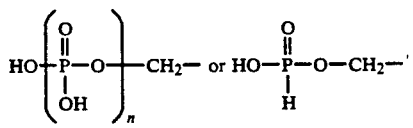

where n is zero, one, two or three;
or Y' and Z together form a cyclic phosphate ester;
Z' is —CN, —CH$_3$, CH$_2$N$_3$ or —CH$_2$J, where J is a halogen atom;
or Z' and Y' together are —CH$_2$O—;
and pharmaceutically acceptable esters, ethers, amides, N-acyl moieties and salts thereof.

In another aspect, the invention relates to pharmaceutical compositions containing a therapeutically effective amount of a compound of Formula I or a pharmaceutically acceptable ester or salt thereof admixed with at least one pharmaceutically acceptable excipient.

In still another aspect, the invention relates to a method of treating infections in a mammal by administering to a mammal in need of such treatment a therapeutically effective amount of a compound of Formula I or a pharmaceutically acceptable esters, ethers, amides, N-acyl moieties and salts thereof.

Another aspect of the invention relates to processes for making compounds of Formula I and the pharmaceutically acceptable esters, ethers, amides, N-acyl moieties and salts thereof.

DETAILED DESCRIPTION

Definitions and General Parameters

The following definitions are set forth to illustrate and define the meaning and scope of the various terms used to describe the invention herein.

The term "lower alkyl" refers to a cyclic, branched or straight chain monovalent alkyl radical of one to six carbon atoms. This term is further exemplified by such radicals as methyl, ethyl, n-propyl, isopropyl, n-butyl, t-butyl, i-butyl or n-hexyl.

The term "lower alkoxy" refers to the group —O—R' where R' is lower alkyl.

The term "halo" refers to fluoro, bromo, chloro and iodo.

The term "aryl" refers to a monovalent unsaturated aromatic carbocyclic radical having a single ring (e.g., phenyl) or two condensed rings (e.g., naphthyl), which can optionally be mono-, di- or tri-substituted, independently, with hydroxy, lower alkyl, lower alkoxy, chloro, fluoro, and/or cyano.

The term "heterocycle" refers to a monovalent saturated or unsaturated carbocyclic radical having at least one hetero atom, such as N, O or S, within the ring, each available position of which can be optionally substituted, independently, with, e.g., hydroxy, oxo, amino, imino, lower alkyl, lower alkoxy, bromo, chloro, fluoro, and/or cyano. Included within this class of substituents are purines and pyrimidines.

The term "heteroaryl" refers to a monovalent aromatic carbocyclic radical having a single ring, or multiple rings condensed, having at least one hetero atom, such as N, O or S, within a single ring or multiple rings, each available position of which can be optionally substituted, independently, with e.g., hydroxy, oxo, amino, imino, lower alkyl, lower alkoxy, bromo, chloro, fluoro, and/or cyano. Included within this class of substituents are purines and pyrimidines.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The term "purine" refers to nitrogenous bicyclic heterocycles, typically including the naturally occurring purines adenine (or 6-aminopurine), hypoxanthine (or 6-oxopurine), guanine (2-amino-6-oxopurine) and xanthine (2,6-dioxopurine). As used herein, the term "purine" also includes moieties that have been derivatized or modified by substitution on the parent skeleton, such as, 2-aminopurine, 8-aminopurine, 2,6-diaminopurine and the like, and/or analogs wherein the parent skeleton is modified by substituting a carbon for a nitrogen or substituting a nitrogen for a carbon, such as, 9-deazapurine, 7-cyano-7-deazapurine, 8-azapurine and the like as known to those skilled in the art. These compounds can be of natural or synthetic origin, isolated or manufactured using exclusively or any combination of chemical, biochemical or enzymological methodology known to those skilled in the art.

The term "pyrimidine" refers to nitrogenous monocyclic heterocycles, typically including the naturally occurring pyrimidines cytosine (4-amino-2-oxopyrimidine), uracil (2,4-dioxopyrimidine) and thymine (5-methyl-2,4-dioxopyrimidine). As used herein, the term pyrimidine also includes moieties that have been derivatized or modified by substitution on the parent skeleton, such as, 5-ethyl-2,4-dioxopyrimidine, 5-propyl-2,4-dioxopyrimidine, 5-fluoromethyl-2,4-dioxopyrimidine, 5-difluoromethyl-2,4-dioxopyrimidine, 5-trifluoromethyl-2,4-dioxopyrimidine, 5-(2-bromo-1-ethenyl)-2,4-dioxopyrimidine, 5-halo-2,4-dioxopyrimidine [including 5-fluoro-2,4-dioxopyrimidine, 5-chloro-2,4-dioxopyrimidine, 5-bromo-2,4-dioxopyrimidine and 5-iodo-2,4-dioxopyrimidine]and the like, and/or analogs wherein the parent skeleton is modified by substituting a carbon for a nitrogen or substituting a nitrogen for a carbon, such as, 4-amino-5-aza-2-oxopyrimidine, 6-aza-5-methyl-2,4-dioxopyrimidine, 6-aza-2,4-dioxopyrimidine, 1-deaza-5-methyl-2,4-dioxopyrimidine and the like as known to those skilled in the art. These compounds can be of natural or synthetic origin, isolated or manufactured using exclusively or any combination of chemical, biochemical or enzymological methodology.

"Thymidine" is by definition 1-(2-deoxy-β-D-erythro-pentofuranosyl)thymine. Thus, by convention, a compound is not referred to as 2'-deoxythymidine even though the X' position corresponding to Formulae I is not OH.

The term "nucleoside" refers to a compound composed of any pentose or modified pentose moiety attached to the natural position of a purine (the 9-position) or pyrimidine (the 1-position) or to the equivalent position in an analog.

The term "nucleotide" refers to a phosphate ester substituted on the 5'-position of a nucleoside. A nucleotide can have one, two or three phosphoryl groups. Thus for any given nucleoside, there can be a monophosphate, diphosphate and triphosphate ester. Further, the mono-phosphoryl moiety may be linked to two positions of the pentose forming the 3'5'-cyclic monophosphate.

The term "protecting group" refers to a chemical group which exhibits the following characteristics. The group must react selectively in good yield to give a protected substrate that is stable to the projected reactions; and the protective group must be selectively removable in good yield by readily available, preferably nontoxic reagents that do not attack the functional group(s) generated in such projected reactions (see, *Protective Groups in Organic Synthesis*, Theodora W. Greene, John Wiley & Sons, 1981, Chapter 1, page 1, The Role of Protective Groups in Organic Synthesis)

Purines are numbered according to the following formula:

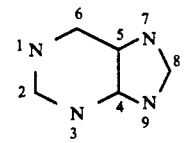

for example, representing guanine where the 2-position is substituted by NH₂ and the 6-position is =O.

Pyrimidines are numbered according to the following formula:

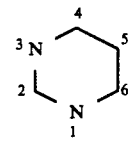

for example, representing thymine where the 2-position is substituted by =O, the 4-position is =O, and the 5-position is —CH₃.

The position of double bonds in purine and pyrimidine substituents will be apparent to those skilled in the art. It should be further understood that the substitution of a hydroxy or amino on the purine and pyrimidine ring also encompasses the tautomeric oxo or imino forms.

The compounds of Formula I may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula I.

The terms "α" and "β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The symbol (±) is used to designate a racemic mixture of individual (+) and (−) isomers.

"Isomers" are different compounds that have the same molecular formula. "Stereoisomers" are isomers that differ only in the way the atoms are arranged in space.

"Enantiomers" are a pair of stereoisomers that are non-superimposable mirror images of each other. A mixture of a pair of enantiomers, in a 1:1 ratio, is a "racemic" mixture.

"Diastereoisomers" are stereoisomers, which are not mirror-images of each other.

"Epimers" are diastereoisomers, which differ only in the configuration of one asymmetric center.

It should be understood that the structures unless otherwise indicated are intended to represent enantiomeric mixtures, either racemic or non-racemic, although for the sake of clarity only one enantiomer is shown.

Certain compounds of the present invention possess asymmetric carbons and may be prepared in either optically active form, including the β-D or the α-L forms, or as a racemic mixture. Unless otherwise specified, the compounds described herein are all in the -D-furanosyl configuration. However, the scope of the subject invention herein is not to be considered limited to this form, but to encompass all other individual optical isomers of the subject compounds and mixtures thereof.

A chemical bond indicated as (∫) refers to the nonspecific stereochemistry of the carbon atoms, e.g. at position 4' of the furanosyl ring (see Reaction Schemes A, C, D, E and G).

When the foregoing structures represents a nucleoside, the positions of the sugar moiety are typically referred to as the prime position (e.g., 4'), whereas the positions on the purine or pyrimidine are not.

In naming the compounds of the instant invention the following numbering systems will be used for the furanosyl ring:

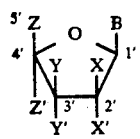

However, in stances where the 4 -carbon is chiral and there results a diastereomeric mixture, then the following numbering system will be used for the furanosyl ring; such that, Z, which is β to the the pentose ring will be designated 4'-β; and Z', which is α to the pentose ring will be designated 4'-α.

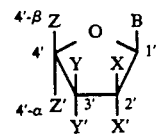

The 3',5'-cyclic phosphate esters are represented by the following formula:

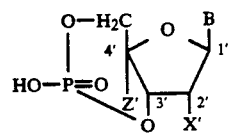

The compounds of the invention will be named using the above-shown numbering system as 4'-substituted nucleosides and derivatives. Some representative compounds are named in the following examples.

The compound of Formula I where B is thymine, X and X' are H, Y is H, Y' is OH, n is zero, and Z' is CN, can be named: 4'-cyanothymidine, or 1- 1-(4'-cyano-2'-deoxy-β-D-erythro-pentofuranosyl)thymine, or 1-(4'-cyano-2'-deoxy-β-D-erythro-pentofuranosyl)-5-methyl-2,4-dioxopyrimidine.

The compound of Formula I where B is thymine, X and X' are H, Y is H, n is zero; and Y' and Z' together are —CH₂—O—;

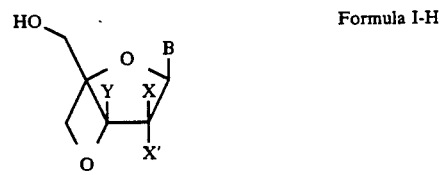

Formula I-H can be named: 1-(1-β-hydroxymethyl-2,6-dioxabicyclo[3.2.0]hept-3β-yl)thymine.

The compound of Formula I where B is thymine, X and X' are H, Y is H, Y' is F, n is zero, and Z' is CH₃, can be named: 3'-deoxy-3'-fluoro-4'-methyl-thymidine, or 1-(2,3-dideoxy-3-fluoro-4-methyl-β-D-erythro-pentofuranosyl)thymine, or 1-(2,3-dideoxy-3-fluoro-4-methyl-β-D-erythro-pentofuranosyl)-5-methyl-2,4-dioxopyrimidine.

The compound of Formula I where B is 2,6-diaminopurine, X and X' are H, Y is H, Y' is OH, n is zero, and Z' is CN, is named 2,6-diamino-9-(4-cyano-2-deoxy-β-D-erythro-pentofuranosyl)purine.

The compound of Formula I where B is uracil, X, X' and Y are H, Y' is OH, n is zero, and Z' is CN, can be named: 2'-deoxy-4'-cyanouridine, or 1-(4-cyano-2-deoxy-β-D-erythro-pentofuranosyl)uracil, or 1-(4-cyano-2-deoxy-β-D-erythro-pentofuranosyl)-2,4-dioxopyrimidine.

Pharmaceutically acceptable esters, amides, ethers and N-acyl moieties include those compounds of Formula I where an oxygen or a nitrogen has been modified, e.g., acylated by the addition of the group —C(═O)—W, wherein W is an alkyl group containing 1 to 20 carbon atoms including adamantyl, aryl, amino, alkylamino, dialkylamino, an alkoxy group containing 1 to 20 carbon atoms, —CH₂—O—CH₃, —CH₂—NH₂, or a group of the formula:

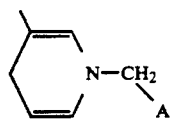

where A is hydrogen, lower alkyl or aryl [such compounds prepared in accordance with the teachings of N. Bodor, et al., Pharmac. Ther., 19, 337-386 (1983), where enhanced blood/brain barrier permeability is suggested for compounds having the subject moiety]. Particularly preferred esters are the adamantoate, the palmitoate and the dihydropyridyl esters. This invention contemplates those compounds of Formula I which are esters as described herein and at the same time are the pharmaceutically acceptable acid addition salts thereof. The invention also contemplates the 3'- and 5'- isopropyl and benzyl ethers of the compounds of Formula I.

A "pharmaceutically acceptable salt" may be any salt derived from an inorganic or organic acid or base. The term "pharmaceutically acceptable anion" refers to the anion of such acid addition salts. The term "pharmaceutically acceptable cation" refers to the cation of such base addition salts. The salt, anion and/or the cation are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The cations are derived from bases, such as, ammonium or (tetraalkyl)ammonium; or from such as alkaline earth hydroxides, including calcium hydroxide, potassium hydroxide, sodium hydroxide, lithium hydroxide, and the like, preferably sodium hydroxide.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylacetamide ("DMA"), dimethylformamide ("DMF"), chloroform, methylene chloride (or dichloromethane), diethyl ether, pyridine and the like]. Unless specified to the contrary, the solvents used in the reactions of the present invention are inert organic solvents.

As used herein, the term "q.s." means adding a quantity sufficient to achieve a stated function, e.g., to bring a solution to a desired volume (e.g., 100 mL).

Unless specified to the contrary, the reactions described herein take place at atmospheric pressure over a temperature range from about −20° C. to about 100° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

As used herein, the term "treatment" or "treating" means any treatment of a disease in a mammal, including:

(i) preventing the disease, that is, avoiding any clinical symptoms of the disease;

(ii) inhibiting the disease, that is, arresting the development or progression of clinical symptoms;

(iii) relieving the disease, that is, causing the repression of clinical symptoms; and/or (iv) eradicating the disease, that is, disposing of the infective agent that is responsible for the disease.

As used herein, the term "effective amount" means a dosage sufficient to provide treatment for the disease state being treated. This will vary depending on the patient, the disease and the treatment being effected.

SYNTHESIS OF THE COMPOUNDS OF FORMULA I

As used in the Reaction Schemes, the substituents B, X', X, Y', Y, Z, Z' and n are the same as described in the Summary of The Invention.

The compounds of Formula I where Y' is OH and Z' is $CH_3$ are prepared as described with reference to Reaction Scheme A. As used in Reaction Scheme A, $R^1$ is an alkoxytrityl group, $R^2$ is a tri-alkyl substituted silyl group, and $R^3$ is an aryl or alky sulfonyl group where Z' is H.

Reaction Scheme A

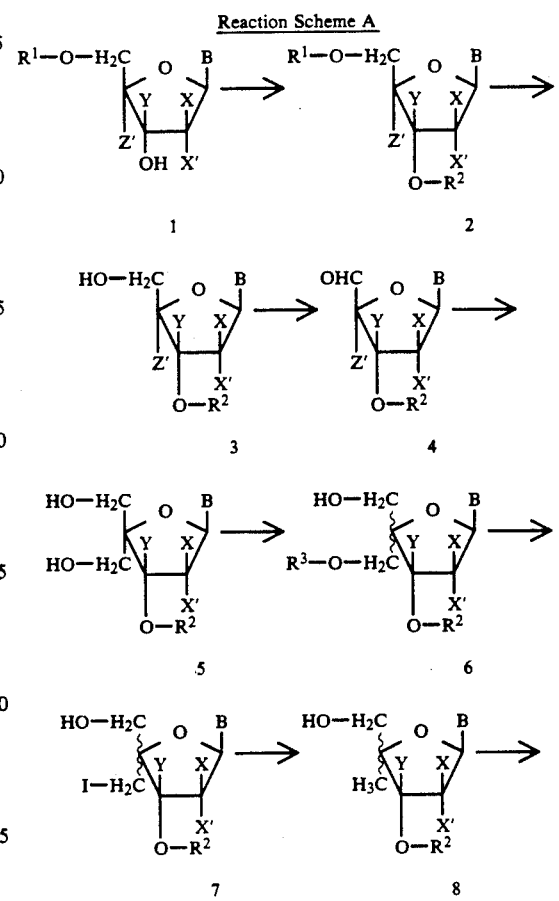

-continued
Reaction Scheme A

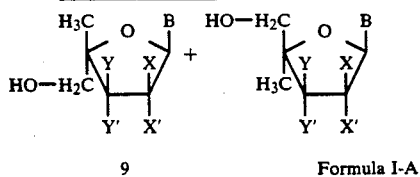

9     Formula I-A

The intermediate compounds of Reaction Scheme A are isolated and purified at each step in the sequence, however, the compounds maybe converted directly to the next compound of the sequence without purification or isolation, except in the instances where it is specifically disclosed that isolation and purification is necessary.

STARTING MATERIAL

Referring to Reaction Scheme A, the starting materials of Formula I are 2'-deoxy-5'-O-dialkoxytrityl-erythro-pentofuranosyl nucleosides (where $R^1$ is dialkoxytrityl) selected from the compounds where B is, for example, 6-aminopurine, 2-amino-6-oxopurine, 2,4-dioxopyrimidine, 5-methyl-2,4-dioxopyrimidine, 4-amino-2-oxopyrimidine, 2,6-diaminopurine, 6-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-halo-2,4-dioxopyrimidine [5-fluoro-2,4-dioxopyrimidine, 5-chloro-2,4-dioxopyrimidine, 5-bromo-2,4-dioxopyrimidine and 5-iodo-2,4-dioxopyrimidine], 5-fluoromethyl-2,4-dioxopyrimidine, 5-difluoromethyl-2,4-dioxopyrimidine, 5-trifluoromethyl-2,4-dioxopyrimidine. Some of the nucleosides may require that functional groups on the heterocycle be protected so as to prevent unwanted reactions, e.g., adenosine and cytidine. The heterocycle is optionally protected according to methods known in the art. Many of the materials are available commercially from such suppliers as, Aldrich Chemical Company, U.S. Biochemicals or Sigma Chemical Company; and where not, they can be easily prepared according to procedures that are well known to the art and published in the literature.

PREPARATION OF INTERMEDIATE 2

To a suspension formed of a compound of Formula 1 in a solvent, such as, DMF, CH$_2$Cl$_2$, THF, preferably, DMF, is added an alkylsilyl halide ($R^2$-X), such as, t-butyldimethylsilyl chloride, triethylsilyl chloride, preferably t-butyldimethylsilyl chloride, a base, such as, imidazole, triethylamine, pyridine, preferably imidazole. The mixture is stirred for a period of 20 to 100 hours, preferably, 65 hours, at a temperature in the range of 0° to 50° C., preferably, 24° C. After removal of the solvent by evaporation, the compound of Formula 2 (where $R^2$ is a tritalkylsilyl group) is isolated and purified by crystallization or chromatography.

PREPARATION OF INTERMEDIATE 3

To a suspension of the compound of Formula 2 in a solvent such as, THF, diethylether, dichloromethane, preferably, THF, is added a mild acid, such as, dil. HCl, H$_2$SO$_4$, or preferably 80% aqueous acetic acid The mixture is stirred for a period of 10 to 30 hours, preferably, 20 hours, at a temperature in the range of 0° to 50° C., preferably, 24° C. The solvents are removed by evaporation and the residue is isolated and purified by chromatography or crystallization.

PREPARATION OF INTERMEDIATE 4

A compound of Formula 3 following the procedures of the compound of Formula 3 following the procedures of the Moffat oxidation, Jones oxidation or Swern and the like. (Swern oxidation—K. Omura and D. Swern, Tetrahedron, 34, 1651 (1978); and Moffat oxidation—Pfitzner, K. E. and Moffat, J, J. American Chem. Soc., 1965, 87, 5661, 5670.)

PREPARATION OF INTERMEDIATE 5

A hydroxymethyl moiety is introduced into the compound of Formula 4 using a Cannizzaro reaction, i.e., reacting the compound of Formula 4 with excess formaldehyde in the presence of a base, such as, sodium hydroxide or potassium carbonate, for a period of 12 hours to 48 hours, preferably, 16 hours; at a temperature in the range of 20° C. to 60° C., preferably, at about room temperature.

PREPARATION OF INTERMEDIATE 6

A compound of Formula 5 is reacted with a n-alkyl or aryl sulfonate, preferably methanesulfonyl chloride or toluenesulfonyl chloride, and a base, preferably triethylamine, or pyridine, in a nonpolar solvent, preferably methylene chloride. After stirring the mixture for a period of about 1 hour to 16 hours, preferably 3 hours; at a temperature in the range of 0° C. to 50° C., preferably at 24° C.; the compound of Formula 6 (where $R^3$ is an n-alkyl- or aryl- sulfonyl group) may be isolated by evaporation of the solvents and extraction of the residue, followed by chromatography (including purification by silica gel or the like), crystallization or lyophilization.

PREPARATION OF INTERMEDIATE 7

The compound of Formula 6 is converted to the iodide using an alkali metal iodide, preferably sodium iodide, in a solvent, such as, 2,5-hexanedione, DMF or DMA, preferably 2,5 hexanedione. After the mixture is stirred for a period of about 4 to 48 hours, preferably 24 hours; at a temperature in the range of 50° C. to 200° C., preferably in the range of 120° to 130° C.; the compounds are isolated by evaporation of solvents and extraction of residue, followed by chromatography (including purification with silica gel or the like), crystallization or lyophilization.

PREPARATION OF INTERMEDIATE 8

The compound of Formula 8 is prepared by reacting the compound of Formula 7 with a reducing agent, such as, lithium aluminum hydride, preferably, H$_2$(g) and 10% palladium on carbon. The mixture is stirred for a period of about 8 hours to 72 hours, preferably, 16 hours; at a temperature in the range of 20° C. to 50° C., preferably at room temperature.

PREPARATION OF COMPOUNDS OF FORMULA I-A

To a solution of the compound of Formula 8 in a solvent such as DMF, THF, preferably, dimethylformamide, is added a fluoride ion source, such as, CsF, KF, (n-butyl)$_4$N$^+$F$^-$, preferably, CsF; at a temperature in the range of 30° C. to 65° C., preferably, in the range of 45° C. to 50° C. for a period of 3 to 48 hours, preferably 12 hours. The compound of Formula I-A is isolated by evaporation of solvents and by extraction of the residue, followed by crystallization, lyophilization or purification by chromatography (including treatment with silica gel or the like). Alternatively, the compound of Formula I-A can be isolated following the isolation procedure described in Reaction Scheme B (see below).

Other compounds of Formula I can be prepared from the compounds of Formula 6 in Reaction Scheme A, as described with reference to Reaction Scheme B.

The intermediate compounds of Reaction Scheme B maybe isolated and purified at each step in the sequence, however, preferably, the compounds are converted directly to the next compound of the sequence without purification or isolation, except in the instances where it is specifically disclosed that isolation and purification is necessary.

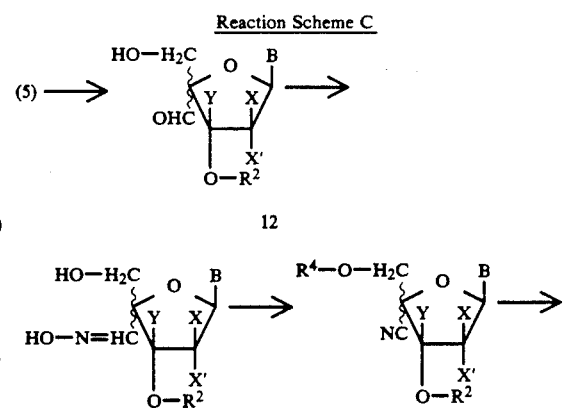

REACTION SCHEME B

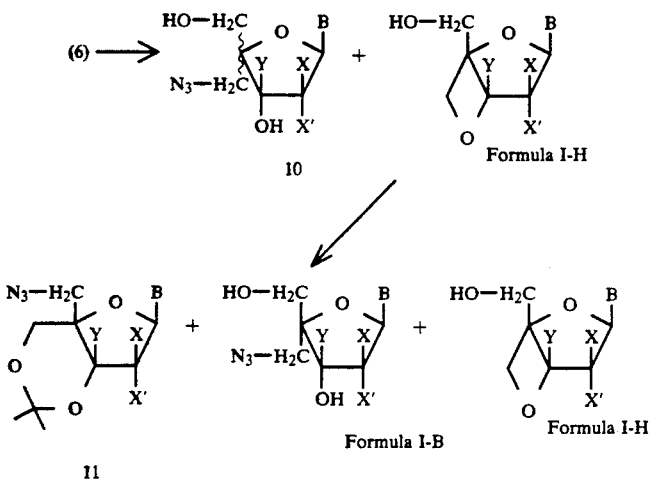

PREPARATION OF THE COMPOUNDS OF FORMULA I-B AND I-H

To a solution of the compound of Formula 6, prepared, e.g., as described in Reaction Scheme A, in a solvent such as, HMPA, DMF, DMA, preferably, HMPA, is added an alkaline azide, such as, sodium azide or lithium azide, preferably, lithium azide. The mixture is stirred for a period of 8 to 24 hours, preferably, 16 hours, at a temperature in the range of 75° to 125° C., preferably, 100° C. The compounds of Formula 10 and I-H are isolated and purified by crystallization or chromatography, preferably, the compounds are taken to the next step without isolation.

ISOLATION OF COMPOUNDS OF FORMULA I-B AND I-H

The mixture of the compounds of Formula 10, I-B and I-H is treated with a solution of 2,2-dimethoxypropane and acid. The reagent reacts with the compound of Formula 10 (where Z' is CH$_2$OH) to form a compound of Formula 11, facilitating its separation from the rest of the mixture. The compounds of Formula I-B and I-H are isolated and purified by silica gel chromatography or the like.

Other compounds of Formula I can be prepared from the compounds of Formula 5 in Reaction Scheme A, as described with reference to Reaction Scheme C. As used in Reaction Scheme C, R$^2$ is a tri-alkyl substituted silyl group, and R$^4$ is an acyl group.

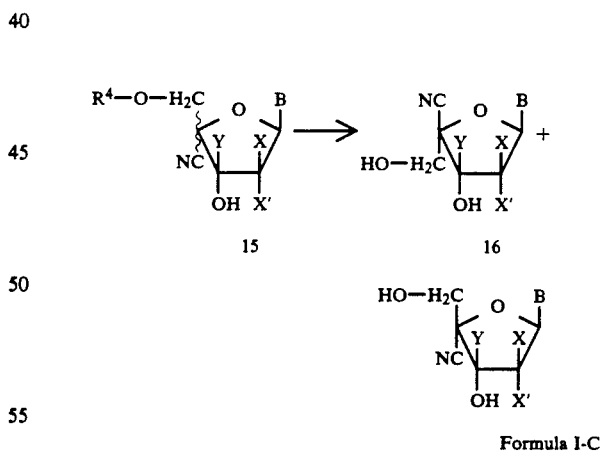

PREPARATION OF INTERMEDIATE 12

A compound of Formula 5, prepared, e.g., as described with reference to Reaction Scheme A, is oxidized following the procedure of Moffat, Jones or Swern, preferably following the Swern procedure.

PREPARATION OF INTERMEDIATES 13

The compound of Formula 12, is treated with HCl·H$_2$NOH in pyridine. The mixture is stirred for 8 to 72 hours, preferably, 16 hours; at a temperature in the range of 0° C. to 50° C., preferably at room temperature.

PREPARATION OF INTERMEDIATES 14

The compound of Formula 13 is treated with a dehydration reagent such as, Ac$_2$O, POCl$_3$, preferably, acetic anhydride, for a period of 16 hours to 96 hours, preferably, 72 hours; at a temperature in the range of 80° C. to 100° C. The compound of Formula 14 (where R$^4$ is an acyl group) can be isolated and purified by chromatography or crystallization, preferably the residue is taken to the next step without purification.

PREPARATION OF INTERMEDIATE 15

To a solution of the compound of Formula 14 in a solvent such as, THF, diethylether, or DMF, preferably, THF, is added a fluoride ion source, such as (n-Bu)$_4$NF, KF, preferably, (n-Bu)$_4$N$^+$F$^-$, and stirred for a period of 1 to 2 hours, preferably, 1½ hours, at a temperature in the range of 0° to 50° C., preferably, 24° C.

PREPARATION OF THE COMPOUNDS OF FORMULA I-C

The compound of Formula I-C is prepared by treating a solution of the compound of Formula 15 with a base, such as, NaOH, NH$_4$OH, preferably, NH$_4$OH; in a solvent, such as, CH$_3$OH, CH$_3$CN, preferably, CH$_3$OH, at a temperature in the range of 30° C. to 65° C., preferably, 24° C., for a period of 1 to 16 hours, preferably 2 hours. The compound of Formula I-C is isolated by evaporation of solvents and by extraction of the residue, followed by crystallization, lyophilization or purification by chromatography (including treatment with silica gel or the like). Alternatively, the compound of Formula I-C can be isolated following the isolation procedure of Reaction Scheme B (see above).

Other compounds of Formula I, particularly where B is cystosine, Z' is cyano and Y' is OH, can be prepared from the compounds of Formula 15 in Reaction Scheme C, as described with reference to Reaction Scheme D.

PREPARATION OF INTERMEDIATE 17

A compound of Formula 15, prepared, e.g., as described with reference to Reaction Scheme C, is treated with an acid chloride or anhydride, such as acetic anhydride, benzoyl chloride, preferably acetic anhydride, in a solvent such as, pyridine, for a period of 4 to 6 hours, preferably, 5 hours, at a temperature in the range of 0° to 50° C., preferably, 24° C. The compound of Formula 17 (where R$^4$ is an aryl or acyl group) is isolated and purified by chromatography or crystallization, preferably the residue is taken to the next step without further purification.

PREPARATION OF INTERMEDIATE 18

The compound of Formula 17 is treated with 1,2,4-triazole and phosphoryl chloride in acetonitrile for a period of 4 to 6 hours, preferably 4 hours, at a temperature in the range of 0° to 50° C., preferably, 24° C. The compound of Formula 18 can be isolated and purified by chromatography or crystallization, preferably the residue is taken to the next step without further purification.

PREPARATION OF COMPOUNDS OF FORMULA I-D

The compound of Formula 18 is treated with aqueous ammonia in a solvent such as, methanol, ethanol, dioxane, preferably, methanol, for a period of 8 to 24 hours, preferably, 16 hours, at a temperature in the range 0° to 50° C., preferably, 24° C. The compound of Formula I-D is isolated by evaporation followed by purification such as silica gel chromatography and crystallization.

REACTION SCHEME E

The compounds of Formula I where Z' is CN, Y' and Y are H, and X and X' are H, can be prepared as described with reference to Reaction Scheme E. As used in Reaction Scheme E, R$^4$ is an acyl group where Z' is H.

STARTING MATERIALS

Referring to Reaction Scheme E, the starting materials of Formula I-E are 2',3'-dideoxy-erythro-pentofuranosyl nucleosides selected from the compounds where B is, for example, 6-aminopurine, 2-amino-6-oxopurine, 2,4-dioxopyrimidine, 5-methyl-2,4-dioxopyrimidine, 4-amino-2-oxopyrimidine, 2,6-diaminopurine, 6-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-halo-2,4-dioxopyrimidine [5-fluoro-2,4-dioxopyrimidine, 5-chloro-2,4-dioxopyrimidine, 5-bromo-2,4-dioxopyrimidine and 5-iodo-2,4-dioxopyrimidine], 5-fluoromethyl-2,4-dioxopyrimidine, 5-difluoromethyl-2,4-dioxopyrimidine, 5-trifluoromethyl-2,4-dioxopyrimidine. Some of the nucleosides may require that functional groups on the heterocycle be protected so as to prevent unwanted reactions, e.g., adenosine and cytidine. The heterocycle is optionally protected according to methods known in the art. Many of the materials are available commercially from such suppliers as, Aldrich Chemical Company, U.S. Biochemicals or Sigma Chemical Company; and where not, they can be easily prepared according to procedures that are well known to the art and published in the literature.

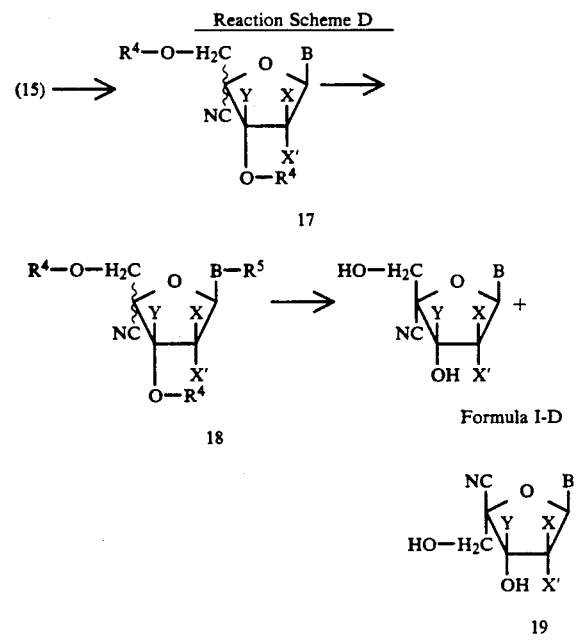

Reaction Scheme D

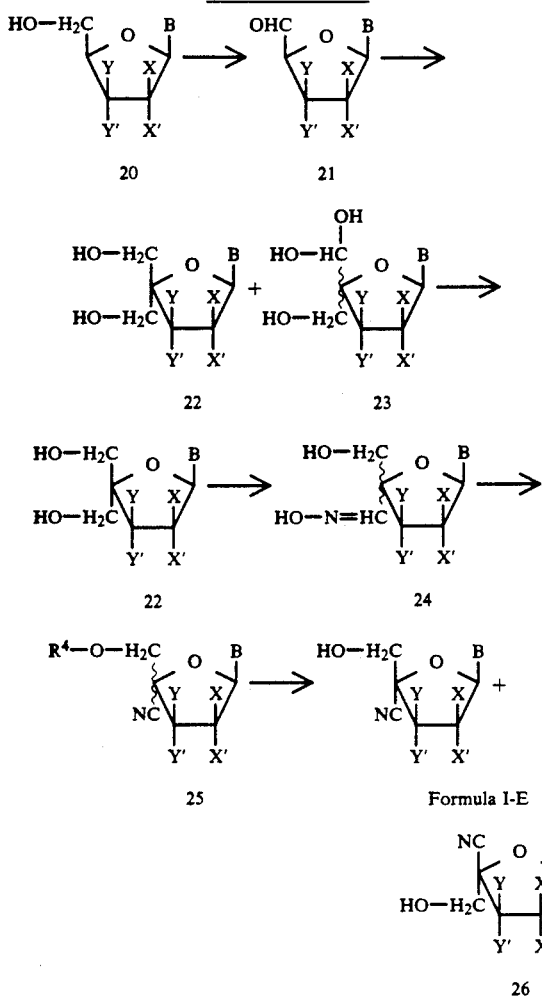

Reaction Scheme E

PREPARATION OF INTERMEDIATE 21

A compound of Formula 21 is prepared by oxidizing a compound of Formula 20 following the procedures of the Moffat oxidation, Jones oxidation or Swern and the like. (Swern oxidation—K. Omura and D. Swern, Tetrahedron, 34, 1651 (1978); and Moffat oxidation—Pfitzner, K. E. and Moffat, J, J. American Chem. Soc., 1965, 87, 5661, 5670.)

PREPARATION OF INTERMEDIATE 22

A compound of Formula 21 is treated with aqueous formaldehyde with a base such as, sodium hydroxide, potassium carbonate, preferably, sodium hydroxide, in a solvent such as, dioxane, THF, preferably, dioxane, for a period of 36 to 60 hours, preferably, 48 hours, at a temperature in the range of 0° to 50° C., preferably, 24° C. The compound of Formula 22 is isolated by removal of the solvents followed by purification by chromatography or crystallization.

The aldehyde hydrate from the above procedure (Formula 23) is treated with a reducing reagent such as, NaBH$_4$, LiAlH$_4$, preferably, NaBH$_4$, in solvent such as, EtOH, MeOH, preferably, EtOH, for a period of 1 to 4 hours, preferably, 3 hours, at a temperature in the range of −78° C. to 24° C., preferably, 0° C. The compound of Formula 22 is isolated by removal of the solvents followed by purification by chromatography or crystallization.

PREPARATION OF INTERMEDIATE 24

A compound of Formula 22 is oxidized following the procedure of Moffat, Jones or Swern, preferably following the Swern procedure. The compound is then treated with HCl·H$_2$NOH in pyridine. The mixture is stirred for 8 to 72 hours, preferably, 16 hours; at a temperature in the range of 0° C. to 50° C., preferably at room temperature. The compound of Formula 24 is isolated by removal of the solvents followed by purification by silica gel chromatography or the like.

PREPARATION OF INTERMEDIATE 25

A compound of the Formula 24 is treated with a dehydration reagent such as, acetic anhydride, POCl$_3$, preferably, acetic anhydride, for a period of 12 to 36 hours, preferably, 24 hours, at a temperature in the range of 75° to 125° C., preferably, 100° C. The compound of Formula 26 is isolated by removal of the solvents and followed by purification by chromatography.

PREPARATION OF THE COMPOUNDS OF FORMULA I-E

A compound of Formula 25 is treated with a base such as, NH$_4$OH, NaOH, preferably, NH$_4$OH, in a solvent such as, methanol, THF, dioxane, preferably, methanol, for a period of 1 to 3 hours, preferably, 2 hours, at a temperature in the range of 0° to 50° C., preferably, 24° C. The compound of Formula I-E is isolated by removal of the solvents and followed by purification by silica gel chromatography or the like, or crystallization.

Other compounds of Formula I, particularly where B is cystosine, Z' is cyano and Y' is H, can be prepared from the compounds of Formula 25 in Reaction Scheme E, as described with reference to Reaction Scheme F. As used in Reaction Scheme A, R$^4$ is an acyl group and R$^5$ is 1,2,4-triazole.

Reaction Scheme F

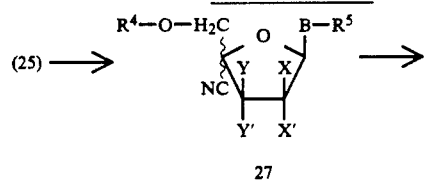

PREPARATION OF INTERMEDIATE 27

A compound of Formula 25, prepared, e.g., as describe in Reaction Scheme E, is treated with 1,2,4-triazole and phosphoryl chloride in acetonitrile for a period of 4 to 6 hours, preferably 4 hours, at a temperature in the range of 0° to 50° C., preferably, 24° C. The compound of Formula 27 (where R$^4$ is an acyl group, and R$^5$ is 1,2,4-triazole) is isolated and purified by chromatography or crystallization.

PREPARATION OF FORMULA I-F

A compound of Formula 27 is treated with aqueous ammonia in a solvent such as, methanol, ethanol, dioxane, preferably, methanol, for a period of 8 to 24 hours, preferably, 16 hours, at a temperature in the range 0 to 50° C., preferably, 24° C. The compound of Formula I-F is isolated by evaporation followed by purification such as silica gel chromatography and crystallization.

The compounds of Formula I-G can be prepared from the compounds of Formula 5 in Reaction Scheme A, as described with reference to Reaction Scheme G. As used in Reaction Scheme G, $R^2$ is a tri-alkyl substituted silyl group, and $R^3$ is an aryl or alky sulfonyl group.

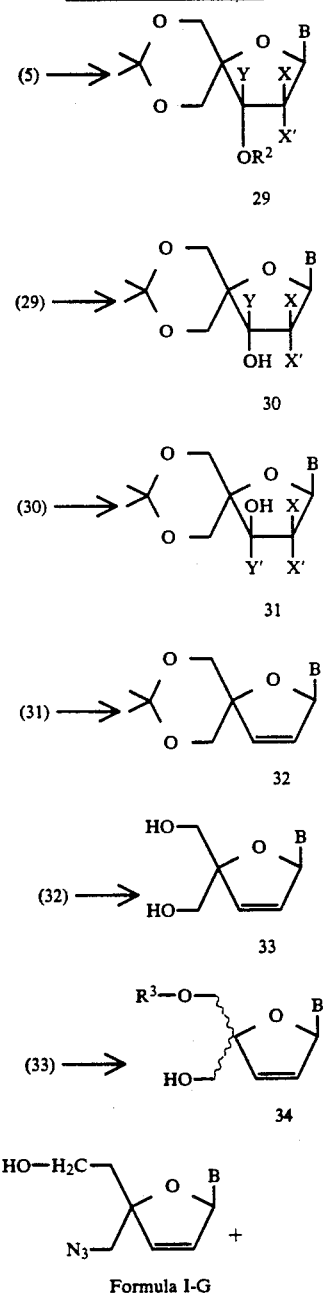
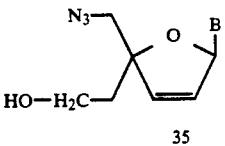

PREPARATION OF INTERMEDIATE 29

A compound of Formula 5, prepared, as described in Reaction Scheme A, is protected as a cyclic acetal or ketal, preferably, acyclic ketal, by reaction with 2,2-dimethoxypropane or acetone, preferably, 2,2-dimethoxypropane, and an acid catalyst, such as, bis(4-nitrophenyl)phosphate hydrate, p-toluenesulfonic acid, preferably, bis(4-nitrophenyl)phosphate hydrate, in a solvent such as, acetone, DMF, preferably, acetone, for a period of 2 to 6 hours, preferably, 4 hours, at a temperature in the range of 0° to 50½° C., preferably, 24½° C. The compound of Formula 29 (where $R^2$ is a tri-alkylsilyl group) is isolated by removal of the solvents followed by purification by chromatography.

PREPARATION OF INTERMEDIATE 30

The compound of Formula 29 is treated with a fluoride ion source such as, tetrabutylammonium fluoride, KF, or the like, preferably, tetrabutylammonium fluoride, in a solvent such as, THF, CH₃CN, DMF, preferably, THF, for a period of 30 to 120 mins, preferably, 90 mins, at a temperature in the range of 0° to 50° C., preferably, 24° C. The compound of Formula 30 is isolated by removal of the solvent followed by purification by chromatography.

PREPARATION OF INTERMEDIATE 31

The compound of Formula 30 is treated with an alkyl or aryl sulfonating reagent such as, methanesulfonyl chloride, p-toluenesulfonyl chloride, preferably, methanesulfonyl chloride, and a base such as, triethylamine, pyridine, preferably, triethylamine, in a solvent such as, $CH_2Cl_2$, THF, $CHCl_3$, preferably, $CH_2Cl_2$, for a period of 30 to 90 mins, preferably, 60 mins, at a temperature in the range of 0° to 50° C., preferably, 24° C. The mesylate obtained from above is then treated with base, such as, NaOH, KOH, preferably NaOH, in a solvent such as, THF, EtOH, DMF, preferably a mixture of THF/EtOH, for a period of 30 to 150 mins, preferably 2 hours, at a temperature in the range of 24° C. to 150° C., preferably in the range of 70° to 80° C. The compound of Formula 31 is isolated by removal of the solvent and purified by silica gel chromatography or the like.

PREPARATION OF INTERMEDIATE 32

The above procedure is repeated, i.e., the compound of Formula 31 is treated according to the preparation of compound 31 from compound 30. The compound of Formula 32 is isolated by removal of solvents followed by purification by silica gel chromatography or the like.

PREPARATION OF INTERMEDIATE 33

To a suspension of the compound of Formula 32 in a solvent such as, THF, diethylether, dichloromethane, preferably, THF, is added a mild acid, such as, dil. HCl or $H_2SO_4$, preferably 80% aqueous acetic acid. The mixture is stirred for a period of 10 to 30 hours, preferably, 20 hours, at a temperature in the range of 0° to 50° C., preferably, 24° C. The solvents are removed by evaporation and the compound of Formula 33 is isolated and purified by chromatography or crystallization.

PREPARATION OF INTERMEDIATE 34

The compound of Formula 33 is treated with an alkyl or aryl sulfonating reagent such as, methanesulfonyl chloride, p-toluenesulfonyl chloride, preferably, methanesulfonyl chloride, and a base such as, triethylamine, pyridine, preferably, triethylamine, in a solvent such as, $CH_2Cl_2$, THF, $CHCl_3$, preferably, $CH_2Cl_2$, for a period of 30 to 90 mins, preferably, 60 mins, at a temperature in the range of 0° to 50° C., preferably, 24° C. The compound of Formula 34 (where $R^3$ is an alkyl- or aryl sulfonyl group) is isolated by removal of the solvent and purified by silica gel chromatography or the like.

PREPARATION OF FORMULA I-G

To a solution of the compound of Formula 34 in a solvent such as, HMPA, DMF, DMA, preferably, HMPA, is added an alkaline azide, such as, sodium azide or lithium azide, preferably, lithium azide. The mixture is stirred for a period 8 to 24 hours, preferably, 16 hours, at a temperature in the range of 75° to 125° C., preferably, 100° C. The compound of Formula I-G is isolated and purified by crystallization or chromatography.

Other compounds of Formula I, particularly where Y' and Z' together are —O—$CH_2$—, can be prepared from the compounds of Formula 29 in Reaction Scheme G, as described with reference to Reaction Scheme H. As used in Reaction Scheme A, $R^6$ is an acyl group.

Reaction Scheme H

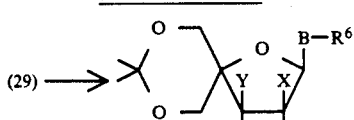

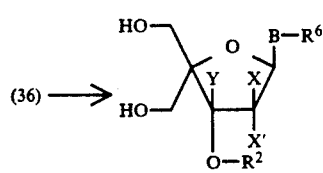

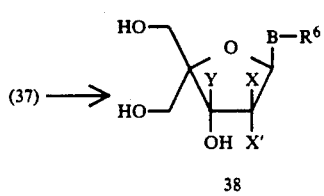

-continued
Reaction Scheme H

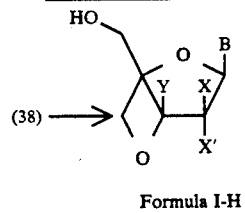

Formula I-H

PREPARATION OF INTERMEDIATE 36

A compound of Formula 29, prepared, e.g., as described in Reaction Scheme G, is treated with an acyl halide such as, benzoyl chloride, acetyl chloride or the like, preferably, benzoyl chloride, an acylation catalyst, such as, 4-dialkylaminopyridines or the like, preferably, 4-dimethylaminopyridine, and a base such as, pyridine, triethylamine or the like, preferably, pyridine, for a period of 8 to 24 hours, preferably, 16 hours, at a temperature range of 0° to 50° C., preferably, 24° C. The compound of Formula 36 (where $R^6$ is an acyl group) is isolated by removal of solvents followed optionally by purification with silica gel chromatography or the like.

PREPARATION OF INTERMEDIATE 37

The compound of Formula 36 is treated with an acidic solution such as, aqueous acetic acid, dilute HCl, dilute $H_2SO_4$, preferably, aqueous acetic acid, in a solvent such as, THF, dioxane, $CH_3CN$, preferably, THF, for a period of 3 to 9 hours, preferably, 6 hours, at a temperature in the range of 25° to 75° C., preferably, 50° C. The compound of Formula 37 is isolated by extraction and removal of the solvents followed by purification by silica gel chromatography or the like.

PREPARATION OF INTERMEDIATE 38

The compound of Formula 37 is treated with a fluoride ion source such as, tetrabutylammonium fluoride, KF, or the like, preferably, tetrabutylammonium fluoride, in a solvent such as, THF, $CH_3CN$, DMF, preferably, THF, for a period of 30 to 120 mins, preferably, 90 mins, at a temperature in the range of 0° to 50° C., preferably, 24° C. The compound of Formula 38 is isolated by removal of the solvent followed by purification by chromatography.

PREPARATION OF FORMULA I-H

The compound of formula 38 is treated with a dehydration reagent mixture such as, triphenylphosphine and diethyl azodicarboxylate (Mitsunobu, O.; Synthesis, 1981, 1) in a solvent such as, THF, dioxane, preferably, THF, for a period of 8 to 24 hours, preferably, 16 hours, at a temperature in the range 10° to 100° C., preferably, 60° C. The solvent is removed and the residue is purified by silica gel chromatography or the like. The residue is treated with a basic solution such as, $NH_4OH$, NaOH, preferably, $NH_4OH$, in a solvent such as, $CH_3OH$, dioxane, preferably, $CH_3OH$, for a period of 2 to 4 hours, preferably, 3 hours, at a temperature in the range of 0° to 50° C., preferably, 24° C. The compound of Formula I-H is isolated by removal of the solvents followed by purification by silica gel chromatography or the like.

PREPARATION OF THE SALTS OF FORMULA I

The pharmaceutically acceptable salts of Formula I are prepared by dissolving a compound of Formula I in a suitable solvent (such as water) adding one to three molar equivalents (preferably one molar equivalent) of an appropriate acid (such as hydrochloric acid) or base (such as an alkaline earth hydroxide, e.g., lithium hydroxide, calcium hydroxide, potassium hydroxide, sodium hydroxide or the like; preferably sodium hydroxide) and stirring. The salt is isolated by lyophilization or by precipitation, using techniques that will be apparent to those skilled in the art.

PREPARATION OF THE ESTERS OF FORMULA I

The pharmaceutically acceptable esters of Formula I are prepared by adding a compound of Formula I and a catalyst (such as 4-dimethylaminopyridine) in pyridine, dropwise to an appropriate acid chloride of the acyl group to be added (such as adamantanecarboxylic acid chloride, palmitic acid chloride, N-methyl-dihydropyrid-3-ylcarboxylic acid chloride or isopropyl acid chloride) either neat or in a solvent (such as methylene chloride, dichloroethane or the like). The reactants are stirred at room temperature for 10 to 24 hours, preferably from 12 to 18 hours The product is isolated by methods well known in the art such as chromatography.

PREPARATION OF THE PHOSPHATE SALTS OF FORMULA I

Phosphorylating agents useful for preparation of the phosphate salts include, for example, phosphoryl chloride, pyrophosphoryl chloride and the like, as will be known to those skilled in the art.

The 5'-monophosphate esters of the nucleosides described herein are prepared starting from the parent nucleoside, for example, using methods described by Imai et al., *Journal of Organic Chemistry*, 34, 1547 (1969).

The 5'-diphosphate esters and 5'-triphosphate esters of the nucleosides described herein are prepared starting from the monophosphates, for example, using methods described by Hoard et al., *Journal of the American Chemical Society*, 87, 1785 (1965).

The 3',5'-cyclicphosphate esters of the nucleosides described herein are prepared starting from the monophosphates, for example, using methods described in Smith et al., *Journal of the American Chemical Society*, 83, 698 (1961).

PREFERRED PROCESSES AND LAST STEPS

The compounds of the present invention can be prepared according to the following last steps (in which non-essential substituents are not discussed, but, will be apparent to those skilled in the art from the reference to the foregoing reaction schemes):

a 2'-deoxy-3,-O-trialkylsilyl-4'-methylnucleoside is contacted with a fluoride ion source to give a compound of Formula I where Z' is methyl;

a 2'-deoxy-3'-O-trialkylsilyl-4'-alkylsulfonyloxynucleoside is contacted with a metal azide to give the compounds of Formula I where Z' is azidomethyl and Formula I-H;

a 2'-deoxy-4'-cyano-5'-O-acylnucleoside is contacted with a base to give the compounds of Formula I where Z' is cyano and Y' is OH;

a 4-(1,2,4-triazol-1-yl)-1-(2-deoxy-4-cyano-3,0-5,0-diacyl-β-D-erythropentofuranosyl)pyrimidin-2(1H)-one is contacted with a base and alcohol to give the compound of Formula I where B is cytosine, Z' is cyano and Y' is OH;

a 2,'3'-dideoxy-4'-cyano-5'-O-acylnucleoside is contacted with a base to give the compound of Formula I where Z' is cyano, and Y' is H;

a 4-(1,2,4-triazol-1-y))-1-(2,3-dideoxy-4-cyano-5-O-acyl-β-D-erythropentofuranosyl)pyrimidin-2(1H)-one is contacted with a base to give the compound of Formula I where B is cytsoine, Z' is cyano and Y' is H;

a 2',3'-dideoxy-2',3'-didehydro-4'-alkylsulfonyloxymethylnucleoside is contacted with a metal azide to give the compound of Formula I where Z' is cyano, and Y' and X' forms a bond; and a N-substituted acyl-4'-hydroxymethylnucleoside is contacted with a dehydration agent to give the compounds of Formula I where Z' and Y' together are —CH₂—O—.

PREFERRED COMPOUNDS

Presently preferred are the compounds of Formula I where B is adenine, guanine, hypoxanthine, uracil, thymine, cytosine, 2,6-diaminopurine, 2-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-fluoro-2,4-dioxopyrimidine, or 5-iodo-2,4-dioxopyrimidine; especially the compounds where B is adenine, guanine, uracil, thymine, or cytosine.

Also preferred are the compounds of Formula I where Z' and Y' together are —CH₂—O—;
especially preferred are the compounds where B is pyrimidine;
also especially preferred are the compounds where Z is the

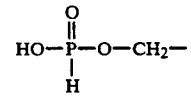

Also preferred are the compounds of Formula I where Z' is cyano;
particularly the compounds where Y' is OH and B is thymine, uracil, cytosine, hypoxanthine, guanine or adenine;
also particularly preferred are the compounds where Y' is H;
Also preferred are the compounds of Formula I where Z' is azidomethyl; particularly where Y' is OH and B is thymine, uracil, cytosine, guanine or adenine;
Also similarly preferred are the compounds of Formula I where Z' is methyl; particularly where Y' is OH and B is thymine, uracil, cytosine, guanine or adenine;
Still other preferred compounds of Formula I are those where B is pyrimidine; particularly where B is thymine, cytosine or uracil.

Most preferred are the compounds 2',3,-dideoxydidehydro-4'-cyanocytosine, 4'-cyanothymidine, and 4'-methylthymidine, 1-(1-β-hydroxymethyl-2,6-dioxabicyclo[3.2.0]hept-3β-yl)thymine, 1-(1-β-hydroxymethyl-2,6-dioxabicyclo[3.2.0]hept-3β-yl)cytosine, especially 4'-cyanothymidine, 2',3'-dideoxy-didehydro-4'-cyanocytosine, 1-(1-β-hydroxymethyl-2,6-dioxabicyclo[3.2.0]hept-3β-yl)thymine, 1-(1-β-hydroxymethyl-2,6-dioxabicyclo[3.2.0]hept-3β-yl)cytosine.

UTILITY, TESTING AND ADMINISTRATION

General Utility

The compounds of this invention are particularly useful for treating viral, bacterial and fungal infections.

Generally, the infections treated with the compounds of the present invention are found in mammals, including: animals such as mice, monkeys and the like; and particularly humans.

The compounds of the present invention, including the pharmaceutically acceptable salts and esters thereof, and the compositions containing them are useful as potent antiviral agents, particularly against human immunodeficiency virus (HIV).

TESTING

In vitro testing for antiviral activity against HIV is done, for example, by the procedures described by Chen et al., *Biochemical Pharmacology*, 36 (24), 4361–4362 (1987), or modifications thereof.

Inhibition of reverse transcriptase and human polymerase is determined by the procedures described by Chen et al., *Molecular Pharmacology*, 25, 441–445 (1984), or as described by Wang et al., *Biochemistry*, 21, 1597–1608 (1982), or by modifications thereof.

Tests for toxicity can be carried out by the procedures described by Diainiak, et al., *British Journal of Haematology*, 69, 229–304 (1988), or as described by Sommadossi, et al., *Agents and Chemotherapy*, 31 (3), 452–454 (1987), or by modifications thereof.

In vivo testing to demonstrate the described antiviral activity of the present compounds is done, for example, by procedures described by Jones et al., *Journal of Virology*, 62 (2), 511–518 (1988), or by modifications thereof.

Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, an acceptable daily dose is of about 0.01 to 150 mg per kilogram body weight of the recipient per day, preferably about 1.5 to 75 mg per kilogram body weight per day, and most preferably about 5 to 30 mg per kilogram body weight per day. Thus, for administration to a 70 kg person, the dosage range would be about 0.7 mg to 10.5 g per day, preferably about 350 mg to 2.1 g per day.

Administration can be via any accepted systemic or local route, for example, via parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc.

For example, in methods of treating AIDS infections, particularly where the compromised subject is suffering from other viral infections, such as, herpes, an active compound of Formula I can be co-administered with one or more agents active in reducing viral infections, such as, acyclovir, ganciclovir, and foscarnet which have been demonstrated to reduce the severity of herpetic viral infections. Co-administration can be in the form of a single formulation (combining, for example, a compound of Formula I and ganciclovir with pharmaceutically acceptable excipients, optionally segregating the two active ingredients in different excipient mixtures designed to independently control their respective release rates and durations) or by independent administration of separate formulations containing the active agents.

If desired, the pharmaceutical composition to be auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

INTRAVENOUS ADMINISTRATION

Intravenous injection has proven to be an important route of administration for antiviral agents. The compounds of the present invention can be administered via this route, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

ORAL ADMINISTRATION

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

LIPOSOMAL FORMULATIONS

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151: 704–710 (1985); Gotfredsen et al., *Biochemical Pharmacology*, 32: 3389–3396 (1983)]; or to the reticuloendothelial system [see Eppstein et al., *Int. J. Immunotherapy*, 2: 115–126 (1986)], to increase duration of drug action [see: Gabizon et al., *Cancer Res.*, 42: 4734 (1982); Eppstein et al., *Delivery Systems for Peptide Drugs*, Eds. S. S. Davis, L. Illum and E. Tomlinson, Plenum Pub. Corp., N.Y., pp. 277–283; C. A. Hunt, *Biochemica et Biophysica Acta.*, 719: 450–463 (1982); and Senior et al., *Biochemica et Biophysica Acta.*, 839: 1–8 (1985)], or to divert a drug away from organs that are particularly sensitive to its toxic effects [see: Weinstein et al., *Pharmac. Ther.*, 24: 207–233 (1983); Olson et al., *Eur. J. Cancer Clin. Oncol.*, 18: 167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. Additionally, viral infections of the eye (such as herpetic keratitis and HIV retinitis) may be treated by use of a sustained release drug delivery system as described in U.S. Pat. No. 4,217,898. The foregoing are incorporated herein by reference.

SUPPOSITORIES

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

LIQUIDS

Liquid pharmaceutically administerable compositions can, for example, be prepared by dissolving, dispersing, etc. an active compound (about 0.5% to about 20%), as: described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following preparations and examples are given to enable those skilled in the art to more clearly understand and to practice the present invention. The examples should not be considered as limiting the scope of the invention, but merely as being illustrative and representative thereof.

PREPARATION 1

1A. Formula 2 Where B is Thymine, X, X' and Y are H t-Butyldimethylsilyl chloride (18 g, 119.6 mM) and imidazole (16 g, 240 mM) were added to a suspension of 5'-O-dimethoxytritylthymidine (44 g, 80.8 mM) in DMF (400 ml) and stirred at room temperature for 65 hours. The solvent was removed by evaporation under pump vacuum (<1 mm) at 75° C. The residue (brownish material) was purified by silica gel flash chromatography on a large column ($CH_2Cl_2$ with 2.5% $CH_3OH$), affording 3'-O-t-butyldimethylsilyl-5'-O-dimethoxytrityl-thymidine (50 g, 76.0 mM), a compound according to Formula 2. MS 658 (M)+

1B. Formula 2 Varying B

By following the procedure of part A and substituting for 5'-O-dimethoxytritylthymidine the following:

2'-deoxy-5'-O-dimethoxytrityladenosine,
2'-deoxy-5'-O-dimethoxytritylguanosine,
2'-deoxy-5'-O-dimethoxytrityluridine,
2'-deoxy-5'-O-dimethoxytritylcytidine,
9-(2-deoxy-5-O-dimethoxytrityl-β-D-erythropentofuranosyl)-2,6-diaminopurine, and
9-(2-deoxy-5-dimethoxytrityl-β-D-erythropentofuranosyl)-6-oxopurine;

there are obtained the following respective compounds:
2'-deoxy-3'-O-t-butyldimethylsilyl-5'-O-dimethoxytrityl adenosine,
2'-deoxy-3'-O-t-butyldimethylsilyl-5'-O-dimethoxytrityl-guanosine,
2'-deoxy-3'-O-t-butyldimethylsilyl-5'-O-dimethoxytrityl-uridine,
2'-deoxy-3'-O-t-butyldimethylsilyl-5'-O-dimethoxytrityl-cytidine,
9-(2-deoxy-3-O-t-butyldimethylsilyl-5-O-dimethoxytrityl-β-D-erythro-pentofuranosyl)-2,6-diaminopurine, and
9-(2-deoxy-3-O-t-butyldimethylsilyl-5-O-dimethoxytrityl-β-D-erythro-pentofuranosyl)-6-oxopurine.

PREPARATION 2

2A. Formula 3 Where B is Thymine, X, X' and Y are H

To a suspension of 3'-O-β-butyldimethylsilyl-5'-O-dimethoxytritylthymidine (50 g, 76.0 mM), prepared, e.g., as described in Preparation 1A, in THF (300 ml), a solution of 80% aqueous acetic acid (100 ml) was added and the mixture stirred for 20 hours at room temperature, resulting in a clear reddish-brown solution. The solvents were removed by evaporation under pump vacuum (<1 mm) at 75° C., yielding a dark brownish oil. The oil was purified by silica gel flash chromatography (large column), eluting first with $CH_2Cl_2$ and then with 2% $CH_3OH$ in $CH_2Cl_2$, gradually increasing to $CH_2Cl_2$ and 3% $CH_3OH$. A light orange/reddish oil was collected affording 3'-O-t-butyldimethylsilylthymidine, a compound of Formula 3.

2B. Formula 3 Varying B

By following the procedure of part A and substituting for 3'-O-t-butyldimethylsilyl-5'-O-dimethoxytrityl thymidine the following:

2'-deoxy-3'-O-t-butyldimethylsilyl-5'-O-dimethoxytrityl-adenosine,
2'-deoxy-3'-O-t-butyldimethylsilyl-5'-O-dimethoxytrityl-guanosine,
2'-deoxy-3'-O-t-butyldimethylsilyl-5'-O-dimethoxytrityl-uridine,
2'-deoxy-3'-O-t-butyldimethylsilyl-5'-O-dimethoxytrityl-cytidine,
9-(2-deoxy-3-O-t-butyldimethylsilyl-5-O-dimethoxytrityl-$\beta$-D-erythro-pentofuranosyl)-2,6-diaminopurine, and
9-(2-deoxy-3-O-t-butyldimethylsilyl-5-O-2-dimethoxytrityl-$\beta$-D-erythro-pentofuranosyl)-6-oxopurine;
2'-deoxy-3'-O-t-butyldimethylsilyladenosine,
2'-deoxy-3'-O-t-butyldimethylsilylguanosine,
2'-deoxy-3'-O-$\beta$-butyldimethylsilyluridine,
2'-deoxy-3'-O-t-butyldimethylsilylcytidine,
9-(2-deoxy-3-O-t-butyldimethylsilyl-$\beta$-D-erythropentofuranosyl)-2,6-diaminopurine, and
9-(2-deoxy-3-O-t-butyldimethylsilyl-$\beta$-D-erythropentofuranosyl)-6-oxopurine.

PREPARATION 3

3A. Formula 4 Where B is Thymine, X, X', and Y are H

To a suspension of 3'-O-t-butyldimethylsilylthymidine (18 g, 50 mM), prepared, e.g., as described in Preparation 2A, in DMSO (dimethylsulfoxide) (150 ml) was added dicyclohexylcarbodiimide (31 g, 150 mM) and the mixture stirred at room temperature (24° C.) until the solid dissolved. Pyridine (4 g, 50 mM) was added followed by trifluoroacetic acid (4 g, 35 mM), which was added in a dropwise fashion with vigorous stirring; upon addition the solution became turbid and warmed up. The solution was stirred at room temperature for 16 hours. Solid residual material was filtered off, water was added to the remaining solution which was extracted with CH$_2$Cl$_2$ six times. The solution was concentrated by removal of solvents by evaporation, and additional solid material was filtered off and washed with CH$_2$Cl$_2$. The solution was once more concentrated by removing the solvents by evaporation, yielding 3'-O-t-butyldimethylsilyl-$\beta$-D-erythro-pentodialdofuranosyl thymine (30 g, 84.7 mM), the compound of Formula 4, as a clear brownish oil containing some DMSO.

3B. Formula 4 Varying B

By following the procedure of part A and substituting for 3'-O-t-butyldimethylsilylthymidine the following:
2'-deoxy-3'-O-t-butyldimethylsilyladenosine,
2'-deoxy-3'-O-t-butyldimethylsilylguanosine,
2'-deoxy-3'-O-t-butyldimethylsilyluridine,
2'-deoxy-3'-O-t-butyldimethylsilylcytidine,
9-(2-deoxy-3-O-t-butyldimethylsilyl-$\beta$-D-erythropentofuranosyl)-2,6-diaminopurine, and
9-(2-deoxy-3-O-t-butyldimethylsilyl-$\beta$-D-erythropentofuranosyl)-6-oxopurine; there are obtained the following respective compounds:

2'-deoxy-3'-O-t-butyldimethylsilyl-$\beta$-D-erythropentodialdofuranosyladenine,
2'-deoxy-3'-O-t-butyldimethylsilyl-$\beta$-D-erythropentodialdofuranosylguanine,
2'-deoxy-3'-O-t-butyldimethylsilyl-$\beta$-D-erythropentodialdofuranosyluracil,
2'-deoxy-3'-O-t-butyldimethylsilyl-$\beta$-D-erythropentodialdofuranosylcytosine,
9-(2-deoxy-3-O-t-butyldimethylsilyly-$\beta$-D-erythropentodialdofuranosyl)-2,6-diaminopurine, and
9-(2-deoxy-3-O-t-butyldimethylsilyly-$\beta$-D-erythropentodialdofuranosyl)-6-oxopurine.

PREPARATION 4

4A. Formula 5 Where B is Thymine, X, X' and Y are H

To a solution of 3'-O-t-butyldimethylsilyl-$\beta$-D-erythro-pentodialdofuranosylthymine (30 g, 84.7 mM), prepared, e.g., as described in Preparation 3, in dioxane (160 ml), a 37% solution of formaldehyde (80 ml) was added followed by the slow addition of 2N NaOH (80 ml). The solution was stirred for 18 hours at room temperature. Solid material was filtered off, water added, and the solution extracted twice with ethyl acetate. The extracts were combined and washed with a sat. NaCl solution. Additional solid material was filtered off and the remaining solution was concentrated by removing the solvents by evaporation. The residue (light brownish material) was purified by silica gel flash chromatography (large column), eluting with CH$_2$Cl$_2$ and followed by CH$_2$Cl$_2$ with 2% methanol, with the concentration being gradually increased to 5% methanol. The compound of Formula 5, 3'-O-t-butyldimethylsilyl-4'-hydroxymethyl-$\beta$-D-erythropentofuranosylthymine (9.5 g, 24.6 mM) was obtained as a light yellowish oil. MS 329 (M-tBu)+.

4B. Formula 3 Varying B

By following the procedure of part A and substituting for 3'-O-t-butyldimethylsilyl-$\beta$-D-erythro-pentodialdofuranosyl- thymine the following:

2'-deoxy-3'-O-t-butyldimethylsilyl-$\beta$-D-erythropentodialdofuranosyladenine,
2'-deoxy-3'-O-t-butyldimethylsilyl-$\beta$-D-erythropentodialdofuranosylguanine,
2'-deoxy-3'-O-t-butyldimethylsilyl-$\beta$-D-erythropentodialdofuranosyluracil,
2'-deoxy-3'-O-t-butyldimethylsilyl-$\beta$-D-erythropentodialdofuranosylcytosine,
9-(2-deoxy-3-O-t-butyldimethylsilyl-$\beta$-D-erythropentodialdofuranosyl)-2,6-diaminopurine, and
9-(2-deoxy-3-O-t-butyldimethylsilyl-$\beta$-D-erythropentodialdofuranosyl)-6-oxopurine; there are obtained the following respective compounds:
2'-deoxy-3'-O-t-butyldimethylsilyl-4'-hydroxymethyladenosine,
2'-deoxy-3'-O-t-butyldimethylsilyl-4'-hydroxymethylguanosine,
2'-deoxy-3'-O-t-butyldimethylsilyl-4'-hydroxymethyluridine,
2'-deoxy-3'-O-t-butyldimethylsilyl-4'-hydroxymethylcytidine,
9-(2-deoxy-3-O-t-butyldimethylsilyl-4-hydroxymethyl-$\beta$-D-erythro-pentofuranosyl)-2,6-diaminopurine, and
9-(2-deoxy-3-O-t-butyldimethylsilyl-4-hydroxymethyl-$\beta$-D-erythro-pentofuranosyl)-6-oxopurine.

PREPARATION 5

5A. Formula 6 Where B is Thymine, X, X' and Y are H

To a solution of 3'-O-β-butyldimethylsilyl-4'-hydroxymethyl-β-D-erythro-pentofuranosylthymine (1.2 g, 3.1 mM), prepared, e.g., as described in Preparation 4, in $CH_2Cl_2$ (20 ml), triethylamine (0.6 g. 6 mM) was added followed by the dropwise addition of mesyl chloride (0.340 g, 3 mM), while the solution was stirred at 24° C. The solution was concentrated by the removal of the solvent by evaporation. The residue was flash chromatographed on silica gel eluting by $CH_2Cl_2$ with 5% methanol, to give a mixture of the 4'-α and 4'-β isomers of 3'-O-t-butyldimethylsilyl-4'-methanesulfonyloxymethylthymidine (1.1 g, 2.4 mM). Calcd. for $C_{18}H_{32}N_2O_8Si$: C, 46.53; H, 6.94; N, 6.05. Found: C, 46.90; H, 7.02; N, 5.78.

5B. Formula 6 Varying B

By following the procedure of part A and substituting for the 4'-α and 4'-β isomers of 3'-O-t-butyldimethylsilyl4'-hydroxymethylthymidine the 4-α and 4'-β isomers of the following:

2'-deoxy-3'-O-t-butyldimethylsilyl-4'-hydroxymethyladenosine,
2'-deoxy-3'-O-t-butyldimethylsilyl-4'-hydroxymethylguanosine,
2'-deoxy-3'-O-t-butyldimethylsilyl-4'-hydroxymethyluridine,
2'-deoxy-3'-O-t-butyldimethylsilyl-4'-hydroxymethylcytidine,
9-(2-deoxy-3-O-t-butyldimethylsilyl-4-hydroxymethyl-D-erythro-pentofuranosyl)-2,6-diaminopurine, and
9-(2-deoxy-3-O-t-butyldimethylsilyl-4-hydroxymethyl-D-β-erythro-pentofuranosyl)-6-oxopurine;

there are obtained the 4'-α and 4'-β isomers of the following respective compounds:

2'-deoxy-3'-O-t-butyldimethylsilyl-4'-methanesulfonyloxymethyladenosine,
2'-deoxy-3'-O-t-butyldimethylsilyl-4'-methanesulfonyloxymethylguanosine,
2'-deoxy-3'-O-t-butyldimethylsilyl-4'-methanesulfonyloxymethyluridine,
2'-deoxy-3'-O-t-butyldimethylsilyl-4'-methanesulfonyloxymethylcytidine,
9-(2-deoxy-3-O-t-butyldimethylsilyl-4'-methanesulfonyloxymethyl-β-D-erythro-pentofuranosyl)-2,6-diaminopurine, and
9-(2-deoxy-3-O-t-butyldimethylsilyl-4'-methanesulfonyloxymethyl-β-D-erythro-pentofuranosyl)-6-oxopurine.

PREPARATION 6

6A. Formula 7 Where B is Thymine, X, X', and Y are H

A solution of the 4'-α and 4'-β isomers of 3'-O-t-butyldimethylsilyl-4'-methanesulfonyloxymethylthymidine (88 mg, 0.18 mM) prepared, e.g., as described in Preparation 5, with NaI (270 mg, 1.8 mM) in 2,5-hexanedione (3 ml) was stirred at 130° C. for 2 hours, at 95° C. for 60 hours and at 130° C. for 24 hours. Solid material was filtered off and the solvent was removed by evaporation under reduced pressure. The residue was purified (twice) by flash chromatography on silica gel. The column was eluted with $CH_2Cl_2+4\%$ $CH_3OH+0.05\%$ acetic acid followed by $CH_2Cl_2+4\%$ $CH_3OH$. The two fractions with identical TLCs and were combined yielding a mixture of the 4'-α and 4'-β isomers of 3'-O--t-butyldimethylsilyl-4'-iodomethylthymidine (70 mg, 0.14 mM), as a light brownish material. MS(CI) 514(M+NH_4)+.

6B. Formula 7 Varying B

By following the procedure of part A and substituting for the 4'-α and 4'-β isomers of 3'-O-t-butyldimethylsilyl-4'-hydroxymethylthymidine the 4'-α and 4'-β isomers of following:

2'-deoxy-3'-O-t-butyldimethylsilyl-4'-methanesulfonyloxymethyladenosine,
2'-deoxy-3'-O-t-butyldimethylsilyl-4'-methanesulfonyloxymethylguanosine,
2'-deoxy-3'-O-t-butyldimethylsilyl-4'-methanesulfonyloxymethyluridine,
2,-deoxy-3'-O-t-butyldimethylsilyl-4'-methanesulfonyloxymethylcytidine,
9-(2-deoxy-3-O-t-butyldimethylsilyl-4'-methanesulfonyloxymethyl-β-D-erythro-pentofuranosyl)-2,6-diaminopurine, and
9-(2-deoxy-3-O-t-butyldimethylsilyl-4'-methanesulfonyloxymethyl-β-D-erythro-pentofuranosyl)-6-oxopurine;

there are obtained the 4'-α and 4'-β isomers of the following respective compounds:

2'-deoxy-3'-O-t-butyldimethylsilyl-4'-iodomethyladenosine,
2'-deoxy-3'-O-t-butyldimethylsilyl-4'-iodomethylguanosine,
2'-deoxy-3'-O-t-butyldimethylsilyl-4'-iodomethyluridine,
2'-deoxy-3'-O-t-butyldimethylsilyl-4'-iodomethylcytidine,
9-(2-deoxy-3-O-t-butyldimethylsilyl-4-iodomethyl -β-D-erythro-pentofuranosyl)-2,6-diaminopurine, and
9-(2-deoxy-3-O-t-butyldimethylsilyl-4-iodomethyl -β-D-erythro-pentofuranosyl)-6-oxopurine.

PREPARATION 7

7A. Formula. 8 Where B is Thymine, X, X', and Y are H

A solution of the 4'-α and 4'-β isomers of 3'-O-t-butyldimethylsilyl-4'-iodomethylthymidine (26 mg, 0.05 mM), prepared, e.g., as described in Preparation 6, 10% Pd-C (palladium on carbon) (15 mg), 1 N NaOH (2 drops) in $CH_3OH$ was stirred under hydrogen atmosphere at 25° C. for 66 hours. The solvent was removed by evaporation under vacuum pressure. The residue was purified by flash silica gel chromatography. The column was eluted with $CH_2Cl_2+5\%$ $CH_3OH$, yielding a mixture of the 4'-α and 4'-β isomers of 3'-O-t-butyldimethylsilyl-4'-methylthymidine (13 mg, 0.035 mM) as a colorless oil. MS 371 (MH)+.

7B. Formula 8 Varying B

By following the procedure of part A and substituting for the 4'-α and 4'-β isomers of 3'-O-t-butyldimethylsilyl'-iodomethylthymidine the 4'-α and 4'-β isomers of following:

2'-deoxy-3'-O-t-butyldimethylsilyl-4'-iodomethyladenosine,
2'-deoxy-3'-O-t-butyldimethylsilyl-4'-iodomethylguanosine,
2'-deoxy-3'-O-t-butyldimethylsilyl-4'-iodomethyluridine,
2'-deoxy-3'-O-t-butyldimethylsilyl-4'-iodomethylcytidine,
9-(2-deoxy-3-O-t-butyldimethylsilyl-4-iodomethyl-β-D-erythro-pentofuranosyl)-2,6-diaminopurine, and
9-(2-deoxy-3-O-t-butyldimethylsilyl-4-iodomethyl-β-D-erythro-pentofuranosyl)-6-oxopurine;

there are obtained the 4'-α and 4'-β isomers of following respective compounds:

2'-deoxy-3'-O-t-butyldimethylsilyl-4'-methyladenosine,
2'-deoxy-3'-O-t-butyldimethylsilyl-4'-methylguanosine,
2'-deoxy-3'-O-t-butyldimethylsilyl-4'-methyluridine,
2'-deoxy-3'-O-t-butyldimethylsilyl-4'-methylcytidine,
9-(2-deoxy-3-O-t-butyldimethylsilyl-4-methyl-β-D-erythro-pentofuranosyl)-2,6-diaminopurine, and
9-(2-deoxy-3-O-t-butyldimethylsilyl-4-methyl-β-D-erythro-pentofuranosyl)-6-oxopurine.

PREPARATION 8

9A. Formula 12 Where B is Thymine X, X' and Y are H

To a solution of $(CCl_3CO)_2O$ (0.275 ml, 1.5 mM) in $CH_2Cl_2$ (0.5 ml) was added slowly a solution of DMSO (0.142 ml, 2 mM) in $CH_2Cl_2$ (1 ml) at $-60°$ C. The mixture was stirred for 15 mins. 3'-O-t-butyldimethylsilyl-4'-hydroxymethylthymidine (0.386 g. 1 mM) (the compound of Formula 5), prepared, for example, as described in Preparation 4, in $CH_2Cl_2$ (1 ml) was added and stirred at $-55°$ C. for 1½ hours. $Et_3N$ (0.42 ml, 3 mM) was added and the reaction mixture was extracted with $CH_2Cl_2$ (3×20 ml). The combined $CH_2Cl_2$ extracts were combined and dried over $Na_2SO_4$. The solvent was removed by evaporation affording the the 4'-α and 4'-β isomers of 3'-O-t-butyldimethylsilyl-4'-formylthymidine (0.380 g).

9B. Formula 12 Varying B

By following the procedure of part A and substituting for 3'-O-t-butyldimethylsilyl-4',4'-di-hydroxymethylthymidine the following:

2'-deoxy-3'-O-t-butyldimethylsilyl-4'-hydroxymethyladenosine,
2'-deoxy-3'-O-t-butyldimethylsilyl-4'-hydroxymethylguanosine,
2'-deoxy-3'-O-t-butyldimethylsilyl-4'-hydroxymethyluridine,
2'-deoxy-3'-O-t-butyldimethylsilyl-4'-hydroxymethylcytidine,
9-(2-deoxy-3-O-t-butyldimethylsilyl-4-hydroxymethylβ-D-erythro-pentofuranosyl)-2,6-diaminopurine, and
9-(2-deoxy-3-O-t-butyldimethylsilyl-4-hydroxymethylβ-D-erythro-pentofuranosyl)-6-oxopurine;
there are obtained the 4'-α and 4'-β isomers of following respective compounds:

2'-deoxy-3'-O-t-butyldimethylsilyl-4'-formyladenosine,
2'-deoxy-3'-O-t-butyldimethylsilyl-4'-formylguanosine,
2'-deoxy-3'-O-t-butyldimethylsilyl-4'-formyluracil,
2'-deoxy-3'-O-t-butyldimethylsilyl-4'-formylcytidine,
9-(2-deoxy-3-O-t-butyldimethylsilyl-4-formyl-β-D-erythro-pentofuranosyl)-2,6-diaminopurine, and
9-(2-deoxy-3-O-t-butyldimethylsilyl-4-formyl-β-D-erythro-pentofuranosyl)-6-oxopurine.

PREPARATION 9

10A. Formula 13 Where B is Thymine X, X' and Y are H

A solution of the 4'-α and 4'-β isomers 3'-O-t-butyldimethylsilyl-4'-formylthymidine (380 mg, 1 mM), the compound of Formula 12, prepared, e.g., as described in Preparation 8, with $H_2NOH$ HCl (110 mg, 1.6 mM) in pyridine (1.5 ml) was stirred at 24° C. for 16 hours. The solvent was removed by evaporation. The residue was partitioned between $H_2O$ (5 ml) and EtOAc (15 ml). The aqueous layer was extracted with EtOAc (10 ml), and the EtOAc fractions were combined. The solvent was removed by evaporation and the residue was purified on a thick silica gel plate (60% EtOAc/hexane), 3'-O-t-butyldimethylsilyl-4'-hydroxyiminomethylthymidine (148 mg, 0.37 mM). MS (399 M+).

10B. Formula 13 Varying B

By following the procedure of part A and substituting for the 4'-α and 4'-β isomers 3'-O-t-butyldimethylsilyl-4'-formyl-thymidine the 4'-α and 4'-β isomers of the following:

2'-deoxy-3'-O-t-butyldimethylsilyl-4'-formyladenosine,
2'-deoxy-3'-O-t-butyldimethylsilyl-4'-formylguanosine,
2'-deoxy-3'-O-t-butyldimethylsilyl-4'-formyluridine,
2'-deoxy-3'-O-t-butyldimethylsilyl-4'-formylcytidine,
9-(2-deoxy-3-O-t-butyldimethylsilyl-4-formyl-β-D-erythro-pentofuranosyl)-2,6-diaminopurine, and
9-(2-deoxy-3-O-t-butyldimethylsilyl-4-formyl-β-D-erythro-pentofuranosyl)-6-oxopurine;

there are obtained the following respective compounds:

2'-deoxy-3'-O-t-butyldimethylsilyl-4'-hydroxyiminomethyladenosine,
2'-deoxy-3'-O-t-butyldimethylsilyl-4'-hydroxyiminomethyl-guanosine,
2'-deoxy-3'-O-t-butyldimethylsilyl-4'-hydroxyiminomethyl-uridine,
2'-deoxy-3'-O-t-butyldimethylsilyl-4'-hydroxyiminomethyl-cytidine,
9-(2-deoxy-3-O-t-butyldimethylsilyl-4-hydroxyiminomethyl-β-D-erythro-pentofuranosyl)-2,6-diaminopurine, and
9-(2-deoxy-3-O-t-butyldimethylsilyl-4-hydroxyiminomethyl-β-D-erythro-pentofuranosyl)-6-oxopurine.

PREPARATION 10

11A. Formula 14 Where B is Thymine X, X' and Y are H

A solution of 3'-O-t-butyldimethylsilyl-4'-hydroxyiminomethylthymidine (1.98 g, 4.95 mM) the compounds of Formula 13, prepared, e.g., as described in Preparation 9) with NaOAc (7 mg, 0.09 mM) in $Ac_2O$ (7 ml) was stirred at 80° C. for 72 hours, allow to cool and treated with 10 g of ice followed by sat. $NaHCO_3$. The solution was extracted $CH_2Cl_2$ (3×100 ml), and the organic phases were combined and dried over $Na_2SO_4$. The solvent was removed by evaporation and the residue was purified by flash column chromatography silica gel eluting with (20% acetone/CH$_2$Cl$_2$) affording 3'-O-t-butyldimethylsilyl-4'-cyano-5'-O-acetylthymidine (1.7 g, 4.0 mM). MP 67°–69° C.

11B. Formula 14 Varying B

By following the procedure of part A and substituting for the 4'-α and 4'-β isomers of 3'-O-t-butyldimethylsilyl-4'-hydroxyiminomethylthymidine the 4'-α and 4'-β isomers of the following:

2'-deoxy-3'-O-t-butyldimethylsilyl-4'-hydroxyiminomethyl adenosine,
2'-deoxy-3'-O-t-butyldimethylsilyl-4'-hydroxyiminomethyl guanosine,
2'-deoxy-3'-O-t-butyldimethylsilyl-4'-hydroxyiminomethyl uridine,
2'-deoxy-3'-O-t-butyldimethylsilyl-4'-hydroxyiminomethyl cytidine,
9-(2-deoxy-3-O-t-butyldimethylsilyl-4-hydroxyiminomethyl-β-D-erythro-pentofuranosyl)-2,6-diaminopurine, and
9-(2-deoxy-3-O-t-butyldimethylsilyl-2 4-hydroxyiminomethyl-β-D-erythro-pentofuranosyl)-6-oxopurine;

there are obtained the following respective compounds:

2'-deoxy-3'-O-t-butyldimethylsilyl-4'-cyano-5'-O-acetyl adenosine,
2'-deoxy-3'-O-t-butyldimethylsilyl-4'-cyano-5'-O-acetyl guanosine,
2'-deoxy-3'-O-t-butyldimethylsilyl-4'-cyano-5'-O-acetyl uracil,
2'-deoxy-3'-O-t-butyldimethylsilyl-4'-cyano-5'-O-acetyl cytidine,
9-(2-deoxy-3-O-t-butyldimethylsilyl-4-cyano-5-O-acetyl-β-D-erythro-pentofuranosyl)-2,6-diaminopurine, and
9-(2-deoxy-3-O-t-butyldimethylsilyl-4-cyano-5-O-acetyl-β-D-erythro-pentofuranosyl)-6-oxopurine.

PREPARATION 11

11A. Formula 15 Where B is Thymine X, X' and Y are H

A solution of 3'-O-t-butyldimethylsilyl-4'-cyano-5'-O-acetylthymidine (1.2 g, 2.84 mM) (the compound of Formula 14), (n-Bu)$_4$NF (g, mM) in THF was stirred at 24° C. for 1½ hours. Dowex 5OH+ resin was added and the solution filtered, the Dowex being further rinsed with THF. The filtrate and the washings were combined, and the solvent removed by evaporation yielding 4'-cyano-5'-O-acetyl-β-D-erythro-pentofuranosyl-thymidine (0.85 g, 2.78 mM).

11B. Formula 15 Varying

By following the procedure of part A and substituting for the 4'-α and 4'-β isomers of 3'-O-t-butyldimethylsilyl-4'-cyano-5'-O-acetylthymidine the 4'-α and 4'-β isomers of the following:

2'-deoxy-3'-O-t-butyldimethylsilyl-4'-cyano-5'-O-acetyladenosine,
2'-deoxy-3'-O-t-butyldimethylsilyl-4'-cyano-5'-O-acetylguanosine,
2'-deoxy-3'-O-t-butyldimethylsilyl-4'-cyano-5'-O-acetyluridine,
2'-deoxy-3'-O-t-butyldimethylsilyl-4'-cyano-5'-O-acetylcytidine,
9-(2-deoxy-3-O-t-butyldimethylsilyl-4-cyano-5-O-acetyl-β-D-erythro-pentofuranosyl)-2,6-diaminopurine, and
9-(2-deoxy-3-O-t-butyldimethylsilyl-4-cyano-5-O-acetyl-β-D-erythro-pentofuranosyl)-6-oxopurine;

there are obtained the following respective compounds:

2'-deoxy-4'-cyano-5'-O-acetyladenosine,
2,-deoxy-4'-cyano-5'-O-acetylguanosine,
2'-deoxy-4'-cyano-5'-O-acetyluridine,
2'-deoxy-4'-cyano-5'-O-acetylcytidine,
9-(2-deoxy-4-cyano-5-O-acetyl-β-D-erythro-pentofuranosyl)- 2,6-diaminopurine, and
9-(2-deoxy-4-cyano-5-O-acetyl-β-D-erythro-pentofuranosyl)-6-oxopurine.

PREPARATION 12

12A. Formula 17 Where B is Uracil and Y' is OH

A solution of 2'-deoxy-4'-cyano-5'-O-acetyl uridine (24 mg, 0.08 mM) and acetic anhydride (20μl) in pyridine (0.2 ml) was stirred at room temperature for 5 h. The solvent was removed by evaporation and the residue was chromatographed on silica gel eluting with 5% CH$_3$OH/CH$_2$Cl$_2$ to give 2'-deoxy-4'-cyano-3'O,5'O-diacetyl uridine (23 mg, 0.07 mM). Accurate Mass Calcd. for C$_{14}$H$_{15}$N$_3$O$_7$: 337.0910. Found: 337.0911

PREPARATION 13

13A. Formula 18 Where B is Cytosine, X, X', Y and Y' are H

Triethylamine (0.13 ml) was added dropwise with a stirred and cooled mixture of 1,2,4-triazole (0.66 g), phosphoryl chloride (20μl) and acetonitrile (0.6 ml). To the resulting mixture was added a solution of 2'-deoxy-4'-cyano-5'-O-acetyl uridine (0.07 g, 0.25 mM) in acetonitrile (0.4 ml) and the reaction mixture was stirred at room temperature for 15 mins. The reaction mixture was filtered and washed with acetonitrile. The solvent was evaporated and the residue was chromatographed on silica gel eluting with 4% CH$_3$OH/CH$_2$Cl$_2$ to give 4-(1,2,4-triazol-1-yl)-1-(2-deoxy-4-cyano-3,O-5,O-diacetyl-β-D-erythro-pentofuranosyl) pyrimidin-2(1H)-one. (0.1 g).

PREPARATION 14

14A. Formula 21 Where B is Thymine, X, X', Y and Y' are H

To a solution of 3'-deoxy-thymidine (0.38 g, 1.68 mM) (3 ml) in DMSO was added DCC (dicyclohexylcarbodiimide) (1.05 g, 5.1 mM) at 24° C. with stirring until dissolved. Pyridine (0.14 ml, 5.1 mM) was added and then TFA (0.092 ml, 1.2 mM) in a dropwise fashion with vigorous stirring, the reaction mixture was stirred at 24° C. for 4 hours.

Oxalic acid (0.38 g, 4.2 mM) was added in 1 ml of MeOH, filtered and washed the residue with EtOAc. The solvents were removed by evaporation and the DMSO removed by vacuum distillation to give 3'-deoxy-β-D-erythro-pentodialdofuranosylthymine, which was used for the next step without further purification.

14B. Formula 21 Varying B

By following the procedure of part A and substituting for 3'-deoxy-β-D-erythro-pentofuranosyl thymine the following:

2',3'-dideoxy-adenosine,
2',3'-dideoxy-guanosine,
2',3'-dideoxy-uridine,
2',3'-dideoxy-cytidine,
9-(2,3-dideoxy-β-D-erythro-pentofuranosyl)-2,6-diaminopurine, and
9-(2,3-dideoxy-β-D-erythro-pentofuranosyl)-6-oxopurine; there are obtained the following respective compounds:

9-(2,3-dideoxy-β-D-erythro-pentodialdofuranosyl)adenine,
9-(2,3-dideoxy-β-D-erythro-pentodialdofuranosyl)guanine,
9-(2,3-dideoxy-β-D-erythro-pentodialdofuranosyl)uracil,
9-(2,3-dideoxy-β-D-erythro-pentodialdofuranosyl)cytosine,
9-(2,3-dideoxy-β-D-erythro-pentodialdofuranosyl)-2,6-diaminopurine, and
9-(2,3-dideoxy-β-D-erythro-pentodialdofuranosyl)-6-oxopurine.

PREPARATION 15

15A. Formula 22 Where B is Thymine, X, X', Y and Y' are H

To the aldehyde (0.38 g, 1.68 mM) obtained from Preparation 14, was added 7 ml of 40% HCHO (aq) and 3.5 ml of 2 N NaOH in 20 ml of dioxane, and stirred at 24° C. for 48 hours. The solution was passed through Dowex 50(H+) resin, and the resin was rinsed with dioxane/H$_2$O (1:1). The solvent was removed from the rinse solution by evaporation. The above procedure (HCHO/NaOH for 48 hours and Dowex filtration) was repeated. The residue was chromatographed on silica gel using 9% MeOH/CH$_2$Cl$_2$ to give the aldehyde hydrate of 3'-deoxy-4'-hydroxymethyl-β-D-erythropentodialdofuranosylthymine, Formula 22 (220 mg, 0.81 mM). To a solution of the aldehyde hydrate obtained from the above (Formula 23) in 10 ml of EtOH, was added NaBH$_4$ (32 mg, 0.84 mM) and stirred at 0° C. for 3 hours. HOAc was added, and the solvents were removed by evaporation. The residue was chromatographed on silica gel (9% MeOH/CH$_2$Cl$_2$) to give 3'-deoxy-4'-hydroxymethyl-β-D-ribofuranosyl thymine (Formula 27) (170 mg, 0.66 mM). Calcd. for C$_{11}$H$_{16}$N$_2$O$_5$·½H$_2$O (260.764): C, 50.67; H, 6.38; N, 10.74. Found: C, 51.04; H, 6.22; N, 10.57.

15B. Formula 22 Varying B

By following the procedure of part A and substituting for 9-(3-deoxy-β-D-erythro-ribodialdofuranosyl)thymine the following:

9-(2,3-dideoxy-β-D-erythro-ribodialdofuranosyl)adenine,
9-(2,3-dideoxy-β-D-erythro-ribodialdofuranosyl)guanine,
9-(2,3-dideoxy-β-D-erythro-ribodialdofuranosyl)uracil,
9-(2,3-dideoxy-β-D-erythro-ribodialdofuranosyl)cytosine,
9-(2,3-dideoxy-β-D-erythro-ribodialdofuranosyl)-2,6-diaminopurine, and
9-(2,3-dideoxy-β-D-erythro-ribodialdofuranosyl)-6-oxopurine;

there are obtained the following respective compounds:

2',3'-dideoxy-4'-hydroxymethyladenosine,
2',3'-dideoxy-4'-hydroxymethylguanosine,
2',3'-dideoxy-4'-hydroxymethyluridine,
2',3'-dideoxy-4'-hydroxymethylcytidine,
9-(2,3-dideoxy-4-hydroxymethyl-β-D-pentofuranosyl)-2,6-diaminopurine, and
9-(2,3-dideoxy-4-hydroxymethyl-β-D-pentofuranosyl)-6-oxopurine.

PREPARATION 16

16A. Formula 24 Where B is Thymine, X, X', Y and Y' are H

To a solution of DMSO (170µl, 2.34 mM) and CH$_2$Cl$_2$ (0.5 ml) at −60° C., was added 135 ml of (COCl)$_2$ in 1 ml of CH$_2$Cl$_2$ dropwise over a period of 5 minutes. After 15 minutes, 3'-deoxy-4'-hydroxymethylthymidine (0.3 g, 1.17 mM), prepared, e.g., as described in Preparation 15, in 0.5 ml DMSO/0.5 ml CH$_2$Cl$_2$ was added slowly and the mixture stirred at −55° C. for 3 hours. After the addition of 0.65 ml TEA, the solution was removed from the cooling bath and allowed to warm to 24° C. at which temperature it was stirred for 15 minutes. The solution was filtered and the solvent was removed by evaporation. The residue was dissolved in pyridine; treated with H$_2$NOH HCl (0.2 g, 2.9 mM), and stirred at 24° C. for 48 hours. The solvent was removed by evaporation and the residue was chromatographed on silica gel using 8% CH$_3$OH/CH$_2$Cl$_2$, yielding a mixture of the 4'-α and 4'-β isomers of 3'-deoxy-4'-hydroxyiminomethylthymidine (140 mg, 0.52 mM).

Calcd. for C$_{11}$H$_{15}$N$_3$O$_5$·½H$_2$O (275.265): C, 47.99; H, 5.74; N, 15.26. Found: C, 47.94; H, 5.62; N, 15.04.

16B. Formula 24 Varying B

By following the procedure of part A and substituting for 3'-deoxy-4'-hydroxymethylthymidine the following:

2',3'-dideoxy-4'-hydroxymethyladenosine,
2',3'-dideoxy-4'-hydroxymethylguanosine,
2',3'-dideoxy-4'-hydroxymethyluridine,
2',3'-dideoxy-4'-hydroxymethylcytidine,
9-(2,3-dideoxy-4-hydroxymethyl-β-D-pentofuranosyl)-2,6-diaminopurine, and
9-(2,3-dideoxy-4-hydroxymethyl-β-D-pentofuranosyl)-6-oxopurine;

there are obtained the 4'-α and 4'-β isomers of the following respective compounds:

2',3'-dideoxy-4'-hydroxyiminomethyladenosine,
2',3'-dideoxy-4'-hydroxyiminomethylguanosine,
2',3'-dideoxy-4'-hydroxyiminomethyluridine,
2',3'-dideoxy-4'-hydroxyiminomethylcytidine,
9-(2,3-dideoxy-4-hydroxyiminomethyl-β-D-pentofuranosyl)-2,6-diaminopurine, and
9-(2,3-dideoxy-4-hydroxyiminomethyl-β-D-pentofuranosyl)-6-oxopurine.

PREPARATION 17

17A. Formula 25 Where B is Thymine, X, X', Y and Y' are H

To a solution of the 4'-α and 4'-β isomers of 3'-deoxy-4'-hydroxyiminomethylthymidine (40 mg, 0.15 mM) (Formula 24) in 0.5 ml acetic anhydride, was added NaOAc (6 mg, 0.07 mM) and stir at 100° C. for 24 hours. The solvent was removed by evaporation and the residue chromatographed on silica gel using 4% $CH_3OH/CH_2Cl_2$, affording the 4'-α and 4'-β isomers of 3'-deoxy-4'-cyano-5'-O-acetylthymidine (32 mg, 0.11 mM).

17B. Formula 25 Varying B

By following the procedure of part A and substituting for 4'-α and 4'-β isomers of 3'-deoxy-4'-hydroxyiminomethyl thymidine the 4'-α and 4'-β isomers of following:

2',3'-dideoxy-4'-hydroxyiminomethyladenosine,
2',3'-dideoxy-4'-hydroxyiminomethylguanosine,
2',3'-dideoxy-4'-hydroxyiminomethyluridine,
2',3'-dideoxy-4'-hydroxyiminomethylcytidine,
9-(2,3-dideoxy-4-hydroxyiminomethyl-β-D-pentofuranosyl)-2,6-diaminopurine, and
9-(2,3-dideoxy-4-hydroxyiminomethyl-β-D-pentofuranosyl)-2-hydroxypurine;

there are obtained the 4'-α and 4'-β isomers of the following respective compounds:

2',3'-dideoxy-4'-cyano-5'-O-acetyladenosine,
2',3'-dideoxy-4'-cyano-5 -O-acetylguanosine,
2',3'-dideoxy-4'-cyano-5'-O-acetyluridine,
2',3'-dideoxy-4'-cyano-5'-O-acetylcytidine,
9-(2,3-dideoxy-4-cyano-5-O-acetyl-β-D-pentofuranosyl)-2,6-diaminopurine, and
9-(2,3-dideoxy-4-cyano-5-O-acetyl-β-D-pentofuranosyl)-2-oxopurine.

PREPARATION 18

18A. Formula 27 Where B is Cytosine, X, X', Y and Y' are H

Triethylamine (0.94 ml, 6.79 mM) was added dropwise to a stirred and cooled mixture of 1,2,4-triazole (0.47 g, 6.81 mM), phosphoryl chloride (0.14 ml, 1.5 mM) and acetonitrile (0.3 ml). To the resulting mixture was added a solution of 2',3'-dideoxy-4'-cyano-5'-O-acetyl uridine (0.07 g, 0.25 mM), prepared, for example, as described in Preparation 17, in acetonitrile (0.2 ml) and the reaction mixture was stirred at room temperature for 15 mins. The reaction mixture was filtered and washed with acetonitrile. The solvent was evaporated and the residue was chromatographed on silica gel eluting with 5% $CH_3OH/CH_2Cl_2$ to give 4-(1,2,4-triazol-1-yl)-1-(2,3-dideoxy-4-cyano-5-O-acetyl-β-D-erythro-pentofuranosyl)pyrimidin-2(1H)-one. (0.067 g, 0.20 mM). Accurate Mass Calcd. for $C_{14}H_{14}H_{14}N_6O_4$: 330.1076. Found: 330.1078.

PREPARATION 19

19A. Formula 29 Where B is Thymine

To a solution of 3'-O-t-butyldimethylsilyl-4'-hydroxymethylthymidine (1 g, 2.61 mM)(the compound of Formula 5, prepared, e.g., as described in Preparation 4) in acetone (10 ml) was added 2,2'-dimethoxypropane (2.6 g, 25 mM) and bis-(4-nitrophenyl)phosphate hydrate (10 mg) and the mixture was stirred at 24° C. for 4 hours. The solvent was removed by evaporation yielding 3'-O-t-butyldimethylsilyl-4'-hydroxymethyl-4',5'-O-isopropylidenethymidine (1.1 g, 2.6 mM).
MP 238.5–242.5; MS 267M+.

19B. Formula 29 Varying B

By following the procedure of part A and substituting for 3'-O-t-butyldimethylsilyl-4'-hydroxymethylthymidine the following:

2'-deoxy-3'-O-t-butyldimethylsilyl-4'-hydroxymethyl adenosine,
2'-deoxy-3'-O-t-butyldimethylsilyl-4'-hydroxymethyl guanosine,
2'-deoxy-3'-O-t-butyldimethylsilyl-4'-hydroxymethyl uridine,
2'-deoxy-3'-O-t-butyldimethylsilyl-4'-hydroxymethyl cytosine
9-(2-deoxy-3-O-t-butyldimethylsilyl-4-hydroxymethyl-β-D-erythro-pentofuranosyl)-2,6-diaminopurine, and
9-(2-deoxy-3-O-t-butyldimethylsilyl-4-hydroxymethyl-β-D-erythro-pentofuranosyl)-6-oxopurine;

there are obtained the following respective compounds:

2'-deoxy-3'-O-t-butyldimethylsilyl-4'-hydroxymethyl-4',5'-O-isopropylideneadenosine,
2'-deoxy-3'-O-t-butyldimethylsilyl-4'-hydroxymethyl-4',5'-O-isopropylideneguanosine,
2'-deoxy-3'-O-t-butyldimethylsilyl-4'-hydroxymethyl-4',5'-O-isopropylideneuridine,
2'-deoxy-3'-O-t-butyldimethylsilyl-4'-hydroxymethyl-4',5'-O-isopropylidenecytidine,
9-(2-deoxy-3-O-t-butyldimethylsilyl-4-hydroxymethyl-4,5-O-isopropylidene-β-D-erythro-pentofuranosyl)-2,6-diaminopurine, and
9-(2-deoxy-3-O-t-butyldimethylsilyl-4-hydroxymethyl-4,5-O-isopropylidene-β-D-erythro-pentofuranosyl)-6-oxopurine.

PREPARATION 20

20A. Formula 30 Where B is Thymine

A solution of 3'-O-t-butyldimethylsilyl-4'-hydroxymethyl-4',5'-O-isopropylidenethymidine (1.1 g, 2.6 mM) with tetrabutylammonium fluoride ($[CH_3(CH_2)_3]_4NF$) in THF (5 ml, 1 M) was stirred at 24° C. for 90 minutes. The solvent was removed by evaporation. The residue was purified by flash column chromatography on silica gel eluting with $CH_2Cl_2+2\%CH_3OH$ and $CH_2Cl_2+5\%CH_3OH$ affording 4'-hydroxymethyl-4',5'-O-isopropylidene thymidine (800 mg, 2.6 mM) as a colorless amorphous solid.

20B. Formula 30 Varying B

By following the procedure of part A and substituting for 3'-O-t-butyldimethylsilyl-4'-hydroxymethyl-4',5'-O-isopropylidene thymidine the following:

2'-deoxy-3'-O-t-butyldimethylsilyl-4'-hydroxymethyl4',5'-O-isopropylideneadenosine,
2'-deoxy-3'-O-t-butyldimethylsilyl-4'-hydroxymethyl4',5'-O-isopropylideneguanosine,
2'-deoxy-3'-O-β-butyldimethylsilyl-4'-hydroxymethyl4',5'-O-isopropylideneuridine, 2'-deoxy-3'-O-t-butyldimethylsilyl-4'-hydroxymethyl4',5'-O-isopropylidenecytidine, 9-(2-deoxy-3-O-t-butyldimethylsilyl-4-hydroxymethyl4,5-O-isopropylidene-β-D-erythro-pentofuranosyl)2,6-diaminopurine, and 9-(2-deoxy-3-O-t-butyldimethylsilyl-4-hydroxymethyl4,5-O-isopropylidene-β-D-erythro-pentofuranosyl)-6-oxopurine;

there are obtained the following respective compounds:

2'-deoxy-4'-hydroxymethyl-4',5'-O-isopropylidenyl adenosine,

2'-deoxy-4'-hydroxymethyl-4',5'-O-isopropylidenyl guanosine,

2'-deoxy-4'-hydroxymethyl-4',5'-O-isopropylidenyluridine,

2'-deoxy-4'-hydroxymethyl-4',5'-O-isopropylidenylcytosine, 9-(2-deoxy-4-hydroxymethyl-4,5-O-isopropylidenyl-β-D-erythro-pentofuranosyl)-2,6-diaminopurine, and 9-(2-deoxy-4-hydroxymethyl-4,5-O-isopropylidenyl-β-D-erythro-pentofuranosyl)-6-oxopurine.

PREPARATION 21

21A. Formula 31 Where B is Thymine

To a solution of 4'-hydroxymethyl-4',5'-O-isopropylidene-thymidine (420 mg, 1.3 mM) in $CH_2Cl_2$ (20 ml) was added methanesulfonyl chloride (300 g, 2.6 mM) and $Et_3N$ (500 mg, 5.2 mM) and the resulting mixture was stirred at 24° C. for 1 hour. 3'-O-mesylate was isolated and eluted by flash chromatography (silica gel) and eluted with $CH_2Cl_2+5\%CH_3OH$. Add 2 N NaOH to the 3'-O-mesylate in EtOH/THF and the mixture was refluxed for 2 hours. The solvents were removed by evaporation under pump vacuum. The residue was purified by flash chromatography (silica gel), eluting with $CH_2Cl_2+2\%$ and $CH_2Cl_2+5\%$ to give 1-(4-hydroxymethyl-4,5-O-isopropylidene-β-D-threo-pentofuranosyl)thymine.

21B. Formula 31 Varying B

By following the procedure of part A and substituting for 4'-hydroxymethyl-4',5'-O-isopropylidenylthymidine the following:

2'-deoxy-4'-hydroxymethyl-4',5'-O-isopropylidenyl-β-D-erythro-pentofuranosyladenine, 2'-deoxy-4'-hydroxymethyl-4',5'-O-isopropylidenyl-β-D-erythro-pentofuranosylguanine, 2'-deoxy-4'-hydroxymethyl-4',5'-O-isopropylidenyl-β-D-erythro-pentofuranosyluracil 2'-deoxy-4'-hydroxymethyl-4',5'-O-isopropylidenyl-β-D-erythro-pentofuranosylcytosine 9-(2-deoxy-4-hydroxymethyl-4,5-O-isopropylidenyl-β-D-erythro-pentofuranosyl)-2,6-diaminopurine, and 9-(2-deoxy-4-hydroxymethyl-4,5-O-isopropylidenyl-β-D-erythro-pentofuranosyl)-2-oxopurine;

there are obtained the following respective compounds:

9-(2-deoxy-4-hydroxymethyl-4,5-O-isopropylidenyl-β-D-threo-pentofuranosyl)adenine, 9-(2-deoxy-4-hydroxymethyl-4,5-O-isopropylidenyl-β-D-threo-pentofuranosyl)9uanine, 1-(2-deoxy-4-hydroxymethyl-4,5-O-isopropylidenyl-β-D-threo-pentofuranosyl)uracil 1-(2-deoxy-4-hydroxymethyl-4,5-O-isopropylidenyl-β-D-threo-pentofuranosyl)cytosine 9-(2-deoxy-4-hydroxymethyl-4,5-O-isopropylidenyl-β-D-threo-pentofuranosyl)-2,6-diaminopurine, and 9-(2-deoxy-4-hydroxymethyl-4,5-O-isopropylidenyl-β-D-threo-pentofuranosyl)-2-oxopurine.

PREPARATION 22

22a. Formula 32 Where Z' is CN, and Y' is H 1-(4-Hydroxymethyl-4,5-O-isopropylidene-β-D-threo-pentofuranosyl)thymine was treated with methanesulfonyl chloride followed by reaction with 2N NaOH according to the procedure described in Preparation 21. After purification by flash column chromatography on silica gel and eluting with $CH_2Cl_2+2\%MeOH$ and $CH_2Cl_2+5\%MeOH$, 3'-deoxy-4'-hydroxymethyl-4',5'-O-isopropylidene thymidin-2'-ene (271 mg) (mp 82°-85° C.) was obtained as an amorphous solid.

22B. Formula 32 Varying B

By following the procedure of part A and substituting for 1-(4-hydroxymethyl-4,5-O-isopropylidene-β-D-threo-pentofuranosyl)thymine the following:

9-(2-deoxy-4-hydroxymethyl-4,5-O-isopropylidenyl-β-D-threo-pentofuranosyl)adenine, 9-(2-deoxy-4-hydroxymethyl-4,5-O-isopropylidenyl-β-D-threo-pentofuranosyl)guanine, 1-(2-deoxy-4-hydroxymethyl-4,5-O-isopropylidenyl-β-D-threo-pentofuranosyl)uracil 1-(2-deoxy-4-hydroxymethyl-4,5-O-isopropylidenyl-β-D-threo-pentofuranosyl)cytosine 9-(2-deoxy-4-hydroxymethyl-4,5-O-isopropylidenyl-β-D-threo-pentofuranosyl)-2,6-diaminopurine, and 9-(2-deoxy-4-hydroxymethyl-4,5-O-isopropylidenyl-β-D-threo-pentofuranosyl)-2-oxopurine;

there are obtained the following respective compounds

2',3'-dideoxy-4'-hydroxymethyl-4',5'-O-isopropylidene adenosin-2'-ene,

2',3'-dideoxy-4'-hydroxymethyl-4',5'-O-isopropylidene guanosin-2'-ene,

2',3'-dideoxy-4'-hydroxymethyl-4',5'-O-isopropylidene uridin-2'-ene,

2',3'-dideoxy-4'-hydroxymethyl-4',5'-O-isopropylidene cytidin-2'-ene, 9-(2,3-dideoxy-4-hydroxymethyl-4,5-O-isopropylidenyl-β-D-erythro-pento-2-furenyl)-2,6-diaminopurine, and 9-(2,3-dideoxy-4-hydroxymethyl-4,5-O-isopropylidenyl-β-D-erythro-pento-2-furenyl)-6-oxopurine.

PREPARATION 23

23A. Formula 33 Where B is Thymine, X, X' and Y are H

To a solution of 3'-deoxy-4'-hydroxymethyl-4',5'-O-isopropylidenethymidin-2'-ene (300 mg, 1 mM) in THF, was added 80% aqueous acetic acid (7 ml) and the mixture was stirred at 24° C. for 18 hours. The solvent was removed by evaporation at 70° C. under pump vacuum, the remaining traces of 80% acetic acid are removed by passing a stream of $N_2$ gas over the compound affording 3'-deoxy-4'-hydroxymethylthymidin-2'-ene (260 mg, 1 mM) as an off-white solid (mp 194°-195° C.).

23B. Formula 33 Varying B

By following the procedure of part A and substituting for 3'-deoxy-4'-hydroxymethyl-4',5'-O-isopropylidenethymidin-2'-ene the following:

2',3'-dideoxy-4'-hydroxymethyl-4',5'-O-isopropylidene adenosin-2'-ene,
2',3'-dideoxy-4'-hydroxymethyl-4',5'-O-isopropylidene guanosin-2'-ene,
2',3'-dideoxy-4'-hydroxymethyl-4',5'-O-isopropylidene uridin-2'-ene,
2',3'-dideoxy-4'-hydroxymethyl-4',5'-O-isopropylidene cytidin-2'-ene,
9-(2,3-dideoxy-4-hydroxymethyl-4,5-O-isopropylidenyl-$\beta$-D-erythro-pento-2-furenyl)-2,6-diaminopurine, and
9-(2,3-dideoxy-4-hydroxymethyl-4,5-O-isopropylidenyl$\beta$-D-erythro-pento-2-furenyl)-6-oxopurine;

there are obtained the following respective compounds:

2',3'-dideoxy-4'-hydroxymethyladenosin-2'-ene,
2',3'-dideoxy-4'-hydroxymethylguanosin-2'-ene,
2',3'-dideoxy-4'-hydroxymethyluridin-2'-ene,
2',3'-dideoxy-4'-hydroxymethylcytidin-2'-ene,
9-(2,3-dideoxy-4-hydroxymethyl-$\beta$-D-erythro-pento-2'-furenyl)-2,6-diaminopurine, and
9-(2,3-dideoxy-4-hydroxymethyl-$\beta$-D-erythro-pento-2'-furenyl)-6-oxopurine.

PREPARATION 24

24A. Formula 34 Where B is Thymine, X, X' and Y are H

To a solution of 3'-deoxy-4'-hydroxymethylthymidin-2'-ene, prepared, e.g., as described in Preparation 23, in CH$_2$Cl$_2$ (20 ml), triethylamine (0.6 g. 6 mM) was added followed by the dropwise addition of mesyl chloride (0.340 g, 3 mM), while the solution was stirred at 24° C. The solution was concentrated by the removal of the solvent by evaporation. The residue was flash chromatographed on silica gel eluting by CH$_2$Cl$_2$ with 5% methanol, to give a mixture of the 4'-$\alpha$ and 4'-$\beta$ isomers of 3'-deoxy-4'-methanesulfonyloxymethylthymidin-2'-ene.

24B. Formula 34 Varying

By following the procedure of part A and substituting for 3'-deoxy-4'-hydroxymethylthymidin-2'-ene the following:

2',3'-dideoxy-4'-hydroxymethyladenosin-2'-ene,
2',3'-dideoxy-4'-hydroxymethylguanosin-2'-ene,
2',3'-dideoxy-4'-hydroxymethyluridin-2'-ene,
2',3'-dideoxy-4'-hydroxymethylcytidin-2'-ene,
9-(2,3-dideoxy-4-hydroxymethyl-$\beta$-D-erythro-pento2'-furenyl)-2,6-diaminopurine, and
9-(2,3-dideoxy-4-hydroxymethyl-$\beta$-D-erythro-pento2'-furenyl)-6-oxopurine;

there are obtained the following respective compounds:

2',3'-dideoxy-4'-methanesulfonyloxymethyladenosin-2'-ene,
2',3'-dideoxymethyl-4'-methanesulfonyloxyguanosin-2'-ene,
2',3'-dideoxy-4'-methanesulfonyloxymethyluridin-2'-ene,
2',3'-dideoxy-4'-methanesulfonyloxymethylcytidin-2'-ene,
9-(2,3-dideoxy-4-methanesulfonyloxymethyl$\beta$-D-erythro-pento-2-furenyl)-2,6-diaminopurine, and
9-(2,3-dideoxy-4-methanesulfonyloxymethyl-$\beta$-D-erythro-pento-2-furenyl)-6-oxopurine.

PREPARATION 25

25A. Formula 36 Where Y' is O and Z' is —CH$_2$— such that Y' and Z' together is —O—CH$_2$—

3'-O-t-butyldimethylsilyl-4'-hydroxymethyl-4',5'-O-isopropylidenethymidine (2.7 g, 6.34 mM), e.g., as described in Preparation 19, was treated with benzoyl chloride (1.5 ml, 12.8 mM) and dimethylaminopyridine (0.1 g, 0.82 mM) in pyridine (20 ml) at 24° C. for 16 hours. The solvent was evaporated and the residue was chromatographed on silica gel eluting with 30% EtOAc/hexane to give N$^3$-benzoyl-3'-O-t-butyldimethylsilyl-4'-hydroxymethyl-4',5'-O-isopropylidene thymidine (3 g, 5.66 mM).

25B. Formula 36 Varying B

By following the procedure of part A and substituting for 3'-O-t-butyldimethylsilyl-4'-hydroxymethyl-4',5'-O-isopropylidenethymidine the following:

2'-deoxy-3'-O-$\beta$-butyldimethylsilyl-4'-hydroxymethyl-4',5'-O-isopropylidene adenosine,
2'-deoxy-3'-O-$\beta$-butyldimethylsilyl-4'-hydroxymethyl-4',5'-O-isopropylidene guanosine,
2'-deoxy-3'-O-$\beta$-butyldimethylsilyl-4'-hydroxymethyl-4',5'-O-isopropylidene uridine,
2'-deoxy-3'-O-t-butyldimethylsilyl-4'-hydroxymethyl-4',5'-O-isopropylidene cytidine,
9-(2-deoxy-3-O-$\beta$-butyldimethylsilyl-4-hydroxymethyl-4,5-O-isopropylidene-$\beta$-D-erythro-pentofuranosyl)-2,6-diaminopurine, and
9-(2-deoxy-3-O-$\beta$-butyldimethylsilyl-4-hydroxymethyl-4,5-O-isopropylidene-$\beta$-D-erythro-pentofuranosyl)-6-oxopurine;

there are obtained the following respective compounds:

N$^6$-benzoyl-2'-deoxy-3'-O-t-butyldimethylsilyl-4'-hydroxymethyl-4',5'-O-isopropylidene adenosine,
N$^1$,N$^2$-dibenzoyl-2'-deoxy-3'-O-$\beta$-butyldimethylsilyl-4'-hydroxymethyl-4',5'-O-isopropylidene guanosine,
N$^3$-benzoyl-2'-deoxy-3'-O-t-butyldimethylsilyl-4'-hydroxymethyl-4',5'-O-isopropylidene uridine,
N$^4$-benzoyl-2'-deoxy-3'-O-t-butyldimethylsilyl-4'-hydroxymethyl-4',5'-O-isopropylidene cytosine,
N$^2$,N$^6$-dibenzoyl-9-(2'-deoxy-3'-O-t-butyldimethylsilyl-4'-hydroxymethyl-4',5'-O-isopropylidenyl-$\beta$-D-erythro-pentofuranosyl)-2,6-diaminopurine, and
N$^3$-benzoyl-9-(2'-deoxy-3'-O-$\beta$-butyldimethylsilyl-4'-hydroxymethyl-4',5'-O-isopropylidenyl$\beta$-D-erythro-pentofuranosyl)-6-oxopurine.

PREPARATION 26

26A. Formula 37 Where Y' is O and Z' is —CH$_2$— such that Y' and Z' together is —O—CH$_2$—

A mixture of N$^3$-benzoyl-3'-O-$\beta$-butyldimethylsilyl-4'-hydroxymethyl-4',5'-O-isopropylidene thymidine (2.5 g, 4.72 mM), 80% aqueous acetic acid (100 ml) and THF (20ML) was stirred at 50° C. for 6 hours. Solvent was evaporation and the residue was dissolved in $CH_2Cl_2$. The dichloromethane solution was washed with water (2x) and brine. After drying over sodium sulfate and evaporation of the solvent, the residue was chromatographed on silica gel eluting with 3% $CH_3OH/CH_2Cl_2$ to give $N^3$-benzoyl-3'-O-β-butyldimethylsilyl-4'-hydroxymethyl thymidine (1.6 g, 3.3 mM). MS 433(M-tBu)+.

26B. Formula 37 Varying B

By following the procedure of part A and substituting for $N^6$-benzoyl-2'-deoxy-3'-O-t-butyldimethylsilyl-4'-hydroxymethyl-4',5'-O-isopropylidene adenosine,
$N^1,N^2$-dibenzoyl-2'-deoxy-3'-O-t-butyldimethylsilyl-4'-hydroxymethyl-4',5'-O-isopropylidene guanosine,
$N^3$-benzoyl-2'-deoxy-3'-O-t-butyldimethylsilyl-4'-hydroxymethyl-4',5'-O-isopropylidene uridine,
$N^4$-benzoyl-2'-deoxy-3'-O-t-butyldimethylsilyl-4'-hydroxymethyl-4',5'-O-isopropylidene cytosine,
$N^2,N^6$-dibenzoyl-9-(2'-deoxy-3'-O-t-butyldimethylsilyl-4'-hydroxymethyl-4',5'-O-isopropylidenylβ-D-erythro-pentofuranosyl)-2,6-diaminopurine, and
$N^3$-benzoyl-9-(2'-deoxy-3'-O-t-butyldimethylsilyl-4'-hydroxymethyl-4',5'-O-isopropylidenylβ-D-erythro-pentofuranosyl)-6-oxopurine;

there are obtained the following respective compounds:

$N^6$-benzoyl-2'-deoxy-3'-O-t-butyldimethylsilyl-4'-hydroxymethyl adenosine,
$N^1,N^2$-dibenzoyl-2'-deoxy-3'-O-t-butyldimethylsilyl-4'-hydroxymethyl guanosine,
$N^3$-benzoyl-2'-deoxy-3'-O-t-butyldimethylsilyl-4'-hydroxymethyl uridine,
$N^4$-benzoyl-2'-deoxy-3'-O-t-butyldimethylsilyl-4'-hydroxymethyl cytosine,
$N^2,N^6$-dibenzoyl-9-(2-deoxy-3-O-t-butyldimethylsilyl-4-hydroxymethyl-β-D-erythro-pentofuranosyl)-2,6-diaminopurine, and
$N^1$-benzoyl-9-(2-deoxy-3-O-t-butyldimethylsilyl-4-hydroxymethyl-β-D-erythro-pentofuranosyl)-6-oxopurine.

PREPARATION 27

27A. Formula 38 Where Y' is O and Z' is —$CH_2$— such that Y' and Z' together is —O—$CH_2$—

A solution of $N^3$-benzoyl-3'-O-t-butyldimethylsilyl-4'-hydroxymethyl thymidine (0.5 g, 1.02 mM) in THF (3 ml) was treated with tetrabutylammonium fluoride in THF (1 M, 1.5 ml, 1.5 mM) at 24° C. for 4 hours. The solvent was removed and the residue was chromatographed on silica gel with 7% $CH_3OH/CH_2Cl_2$ to give $N^3$-benzoyl-4'-hydroxymethyl thymidine (0.3 g, 0.83 mM).

27B. Formula 38 Varying B

By following the procedure of part A and substituting for $N^3$-benzoyl-3'-O-t-butyldimethylsilyl-4'-hydroxymethyl thymidine the following:

$N^6$-benzoyl-2'-deoxy-3'-O-β-butyldimethylsilyl-4'-hydroxymethyl adenosine,
$N^1,N^2$-dibenzoyl-2'-deoxy-3'-O-t-butyldimethylsilyl-4'-hydroxymethyl guanosine,
$N^3$-benzoyl-2'-deoxy-3'-O-t-butyldimethylsilyl-4'-hydroxymethyl uridine,
$N^4$-benzoyl-2'-deoxy-3'-O-t-butyldimethylsilyl-4'-hydroxymethyl cytosine,
$N^2,N^6$-dibenzoyl-9-(2-deoxy-3-O-t-butyldimethylsilyl-4-hydroxymethyl-β-D-erythro-pentofuranosyl)-2,6-diaminopurine, and
$N^1$-benzoyl-9-(2-deoxy-3-O-t-butyldimethylsilyl-4-hydroxymethyl-β-D-erythro-pentofuranosyl)-6-oxopurine;

there are obtained the following respective compounds:

$N^6$-benzoyl-2'-deoxy-4'-hydroxymethyl adenosine,
$N^1,N^2$-benzoyl-2'-deoxy-4'-hydroxymethyl guanosine,
$N^3$-benzoyl-2'-deoxy-4'-hydroxymethyl uridine,
$N^4$-benzoyl-2'-deoxy-4'-hydroxymethyl cytosine,
$N^2,N^6$-dibenzoyl-9-(2-deoxy-4-hydroxymethyl-β-D-erythro-pentofuranosyl)-2,6-diaminopurine, and
$N^1$-benzoyl-9-(2-deoxy-4-hydroxymethyl-β-D-erythro-pentofuranosyl)-6-oxopurine.

EXAMPLE 1

4'-methylthymidine

A. Formula I Where B is Thymine, Z' is CH3, Y' is OH, X, X' and Y are H

To a solution of the 4'-α and 4'-β isomers of 3'-O-t-butyldimethylsilyl-4'-methylmidine (20 mg, 0.054 mM), prepared, e.g., as described in Preparation 7, in DMF (1 ml), was added CsF (15 mg, 0.1 mM) and the mixture was stirred at 47° C. for 18 hours. The solution was concentrated by removal of the solvents by evaporation under pump vacuum. The residue was purified by flash chromatography on silica gel, eluting with $CH_2Cl_2 + 10\%$ EtOH to yield a mixture of the 4'-α and 4'-β isomers of 4'-methylthymidine (14 mg, 0.054 mM). Chromatography of this mixture on thick silica gel plates with 10%/$CH_3OH/CH_2Cl_2$ afforded 4'-methylthymidine (9 mg, 0.035 mM). Calcd. for $C_{11}H_{16}N_2O_5$ (256.26): C, 51.55; H, 6.29; N, 10.93. Found: C, 51.29; H, 6.32; N, 10.88.

B. Formula I Varying B

By following the procedure of part A and substituting for the 4'-α and 4'-β isomers of 3'-O-t-butyldimethylsilyl-4'-methylthymidine the 4'-α and 4'-β isomers of following:

2,-deoxy-3'-O-t-butyldimethylsilyl-4'-methyladenosine,
2'-deoxy-3'-O-t-butyldimethylsilyl-4'-methylguanosine,
2'-deoxy-3'-O-t-butyldimethylsilyl-4'-methyluridine,
2'-deoxy-3'-O-t-butyldimethylsilyl-4'-methylcytidine,
9-(2-deoxy-3-O-β-butyldimethylsilyl-4-methyl-β-D-erythro-pentofuranosyl)-2,6-diaminopurine, and
9-(2-deoxy-3-O-t-butyldimethylsilyl-4-methyl-β-D-erythro-pentofuranosyl)-6-oxopurine;

there are obtained the 4'-α and 4'-β isomers of following respective compounds:

2'-deoxy-4'-methyl adenosine,
2'-deoxy-4'-methyl guanosine,
2'-deoxy-4'-methyl uridine,
2'-deoxy-4'-methyl cytidine,
9-(2-deoxy-4-methyl-β-D-erythro-pentofuranosyl)-2,6-diaminopurine, and 9-(2-deoxy-4-methyl-β-D-erythro-pentofuranosyl)-6-oxopurine.

EXAMPLE 2

4'-Azidomethylthymidine and 3-β-(1-β-hydroxymethyl-2,6-dioxabicyclo[3.2.0]hept-3β-yl)thymine A. Formula I Where B is Thymine, Z' is $N_3$—$CH_2$, X, X', and Y are H To a solution of the 4'-α and 4'-β isomers of 3'-O-t-butyldimethylsilyl-4'-methanesulfonyloxymethylthymidine (5.9 g, 12.7 mM), prepared, e.g., as described in Preparation 5, in HMPA (hexamethylphosphoramide) (40 ml) was added $LiN_3$ (5 g, 102 mM) and the mixture was stirred at 100° C. for 16 hours. The $LiN_3$ is removed by passing the reaction solution through a short flash silica gel pad (3 inches) in a large column. The column was eluted with $CH_2Cl_2$+5% $CH_3OH$ followed by $CH_2Cl_2$+10% $CH_3OH$. The fractions were concentrated by removal of solvents by evaporation under pump vacuum, yielding a clear yellowish solution. Excess hexane was added to the solution with vigorous stirring, the hexane was then decanted off. The residue was purified by column chromatography, eluting with $CH_2Cl_2$+10% $CH_3OH$, yielding a mixture (3.2 g) of the 4'-α and 4'-β isomers of 4'-azidomethylthymidine (the compounds of Formula 10 and Formula I-B) and 1-(1-β-hydroxymethyl-2,6-dioxabicyclo[3.2.0]hept-3β-yl)thymine (the compound of Formula I-H).

B. Formula I Varying B

By following the procedure of part A and substituting for the 4'-α and 4'-β isomers of 3'-O-t-butyldimethylsilyl-4'-methanesulfonyloxymethylthymidine with the 4'-α and 4'-β isomers of following:

2'-deoxy-3'-O-t-butyldimethylsilyl-4'-methanesulfonyloxymethyladenosine,
2-deoxy-3'-O-β-butyldimethylsilyl-4'-methanesulfonyloxymethylguanosine,
2'-deoxy-3'-O-β-butyldimethylsilyl-4'-methanesulfonyloxymethyluridine,
2'-deoxy-3'-O-β-butyldimethylsilyl-4'-methanesulfonyloxymethylcytidine,
9-(2-deoxy-3-O-β-butyldimethylsilyl-4'-methanesulfonyloxymethyl-β-D-erythro-pentofuranosyl)-2,6-diaminopurine, and
9-(2-deoxy-3-O-β-butyldimethylsilyl-4-methane sulfonyloxymethyl-β-D-erythro-pentofuranosyl)-6-oxopurine;

there are obtained the 4'-α and 4'-β isomers and 2,6-dioxabicyclo[3 2.0]hept-3β-yl compound of the following respective compounds:

2'-deoxy-4,-azidomethyladenosine and 9-(1-β-hydroxymethyl-2,6-dioxabicyclo[3.2.0]hept-3β-yl)adenine,
2'-deoxy-4'-azidomethylguanosine and 9(1-β-hydroxymethyl-2,6-dioxabicyclo[3.2.0]hept-3β-yl)guanine,
2'-deoxy-4'-azidomethyluridine and 1-(1-β-hydroxymethyl-2,6-dioxabicyclo[3.2.0]hept-3β-yl)uracil,
2'-deoxy-4'-azidomethylcytidine and 1-(1-(1-β-hydroxymethyl-2,6-dioxabicyclo[3.2.0]hept-3β-yl)cytosine,
9-(2-deoxy-4-azidomethyl-β-D-erythro-pentofuranosyl)2,6-diaminopurine and
9-(1-β-hydroxymethyl-2,6-dioxabicyclo[3.2.0]-hept-3β-yl)-2,6-diaminopurine, and
9-(2-deoxy-4-azidomethyl-β-D-erythro-pentofuranosyl)-6-oxopurine and
9(1-β-hydroxymethyl-2,6-dioxabicyclo[3 2.0]hept-3β-yl)-6-oxopurine.

EXAMPLE 3

Isolation of 4'-Azidomethylthymidine and 3-β-(1-β-hvdroxymethyl-2,6-dioxabicyclo3.2.01hept-3β-yl)thymine A. Formula I Where B is Thymine, Z' is $N_3CH_2$, Y' is OH, X, X' and Y are H To a mixture of the 4'-α and 4'-β isomers of 4'-azidomethylthymidine and 1-(1-β-hydroxymethyl-2,6-dioxabicyclo[3.2.0]hept-3β-yl)thymine (3 g), prepared, e.g., as described in Example 2, in acetone (40 ml) was added dimethoxypropane (10 ml) and bis(4-nitrophenyl)phosphate (0.17 g) and the mixture is stirred at 24° C. for 4 hours. The solution was concentrated by removal of solvents by evaporation under pump vacuum. The residue was passed through silica gel flash columns eluting with $CH_2Cl_2$+5% $CH_3OH$ followed by $CH_2Cl_2$+10% $CH_3OH$, yielding the compound of Formula I-B, 4'-azidomethylthymidine (0.51 g) Calcd. for $C_{11}H_{15}N_5O_5$ (297.273): C, 44.05; H, 5.09; N, 23,56. Found: C, 43.90; H, 5.36; N, 23.77. and the compound of Formula I-H, 1-(1-β-hydroxymethyl-2,6-dioxabicyclo[3.2.0]hept-3β-yl)thymine (0.48 g) (mp. 207°-208° C.). Calcd. for $C_{11}H_{14}N_2O_5$ (254.24): C, 51.97; H, 5.55; N, 11.02. Found: C, 51.99; H, 5.52; N, 11.04., a compound of Formula I-H.

B. Formula I Varying B

By following the procedure of part A and substituting for the 4'-α and 4'-β isomers of 4'-azidomethylthymidine with the 4'-α and 4'-β isomers of following:

2'-deoxy-4'-azidomethyladenosine,
2'-deoxy-4'-azidomethylguanosine,
2'-deoxy-4'-azidomethyluridine,
2'-deoxy-4'-azidomethylcytidine,
9-(2-deoxy-4-azidomethyl-β-D-erythro-pentofuranosyl)2,6-diaminopurine, and
9-(2-deoxy-4-azidomethyl-β-D-erythro-pentofuranosyl)-6-oxopurine;

there are obtained the following respective compounds corresponding to Formulas I and I-H:

2'-deoxy-4'-azidomethyladenosine and 9-(1-β-hydroxymethyl-2,6-dioxabicyclo[3.2.0]hept-3β-yl)adenine,
2'-deoxy-4'-azidomethylguanosine and 9-(1-β-hydroxymethyl-2,6-dioxabicyclo[3.2.0]hept-3β-yl)guanine,
2'-deoxy-4'-azidomethyluridine and 1-(1-β-hydroxymethyl-2,6-dioxabicyclo[3.2.0]hept-3β-yl)uracil,
2'-deoxy-4'-azidomethylcytidine and 1-(1-β-hydroxymethyl-2,6-dioxabicyclo[3.2.0]hept-3β-yl)cytidine,
9-(2-deoxy-4-azidomethyl-β-D-erythro-pentofuranosyl)-2,6-diaminopurine and 9-(1-β-hydroxymethyl-2,6-dioxabicyclo[3.2.0]hept-3β-yl)-2,6-diaminopurine, and
9-(2-deoxy-4-azidomethyl-β-D-erythro-pentofuranosyl)-6-oxopurine and 9-(1-β-hydroxymethyl-2,6-dioxabicyclo3.2.0]hept-3β-yl)-6-oxopurine.

EXAMPLE 4

4'-cyanothymidine

A. Formula I Where B is Thymine, Z' is cyano, X, X' and Y are H

A solution of 4'-cyano-5'-O-acetylthymidine (0.85 g, 2.76 mM) and NH4OH (15 ml) in CH3OH (15 ml) was stirred at 24° C. for 2 hours. The solvent was removed by evaporation under pump vacuum. The residue was purified by flash chromatography on silica gel eluting with (7% CH3OH/CH2Cl2) and by preparative chromatography TLC affording 4'-cyanothymidine (300 mg, 1.12 mM). mp 238.5° C. to 242.5° C.

B. Formula I Varying B

By following the procedure of part A and substituting for 4'-cyano-5'-O-acetylthymidine with the following:

2'-deoxy-4'-cyano-5'-O-acetyladenosine,
2'-deoxy-4'-cyano-5,-O-acetylguanosine,
2'-deoxy-4'-cyano-5'-O-acetyluridine,
2'-deoxy-4'-cyano-5'-O-acetylcytidine,
9-(2-deoxy-4-cyano-5-O-acetyl-$\beta$-D-erythro-pentofuranosyl)- 2,6-diaminopurine, and
9-(2-deoxy-4-cyano-5-O-acetyl-$\beta$-D-erythro-pentofuranosyl)-6-oxopurine;

there are obtained the following respective compounds:

2'-deoxy-4'-cyanoadenosine,
2'-deoxy-4'-cyanoguanosine,
2'-deoxy-4'-cyanouridine,
2'-deoxy-4,-cyanocytidine,
9-(2-deoxy-4-cyano-$\beta$-D-erythro-pentofuranosyl)-2,6-diaminopurine, and
9-(2-deoxy-4-cyano-$\beta$-D-erythro-pentofuranosyl)-6-oxopurine.

EXAMPLE 5

2'-deoxy-4'-cyano cytidine

A. Formula I Where B is cytosine, and Y' is OH 4-(1,2,4-triazol-1-yl)-1-(2-deoxy-4-cyano-3,O-5,O-diacetyl-$\beta$-D-erythropentofuranosyl) pyrimidin-2(1H)-one (10 mg) was treated with aqueous ammonia (0.2 ml) and methanol (0.2 ml) at room temperature for 16 hours. The solvent was evaporated and the residue was chromatographed on silica gel (Preparative TLC) eluting with EtoAc/isopropyl alcohol/H2O (6:2:8:) to give 2'-deoxy-4'-cyano cytidine (9 mg) MS 253(MH+).

EXAMPLE 6

3'-deoxy-4'-cyanothymidine

A. Formula I Where B is Thymine, Z' is Cyano, X, X', Y' and Y are H

The 4'-$\alpha$ and 4'-$\beta$ isomers of 3'-deoxy-4'-cyano-5'-O-acetylthymidine (Formula 30) (26 mg, 0.09 mM) is dissolved in 0.2 ml NH4OH/0.2 ml CH3OH and stirred at 24° C. for 2 hours. The solvent is removed by evaporation and the residue chromatographed on silica gel (Preparative TLC, 2 plates, 1000 microns) using 1% CH3OH/EtOAc with 0.8% NH4OH, affording the 4'-$\alpha$ and 4'-$\beta$ isomers of 3'-deoxy-4'-cyanothymidine, 6 mg, 0.024 mM, MS 251 (M+); and 11 mg, 0.044 mM, MS 251(M+), respectively.

B. Formula I Varying B

By following the procedure of part A and substituting for 4'-$\alpha$ and 4'-$\beta$ isomers of 3',5'-dideoxy-4'-cyano-5'-acetylthymidine the following:

2',3'-dideoxy-4'-cyano-5'-O-acetyladenosine,
2',3'-dideoxy-4'-cyano-5'-O-acetylguanosine,
2',3'-dideoxy-4'-cyano-5'-O-acetyluridine,
2',3'-dideoxy-4'-cyano-5'-O-acetylcytidine,
9-(2,3-dideoxy-4-cyano-5-O-acetyl-$\beta$-D-pentofuranosyl)-2,6-diaminopurine, and
9-(2,3-dideoxy-4-cyano-5-O-acetyl-$\beta$-D-pentofuranosyl)-2-oxopurine;

there are obtained the following respective compounds:

2',3'-dideoxy-4'-cyanoadenosine,
2',3'-dideoxy-4'-cyanoguanosine,
2',3'-dideoxy-4'-cyanouridine,
2',3'-dideoxy-4'-cyanocytidine,
9-(2,3-dideoxy-4-cyano-$\beta$-D-pentofuranosyl)-2,6-diaminopurine, and
9-(2,3-dideoxy-4-cyano-$\beta$-D-pentofuranosyl)-6-oxopurine.

EXAMPLE 7

2',3'-dideoxy-4'-cyano cytidine

A. Formula I Where B is Cytosine, X, X', Y and Y' are H 4-(1,2,4-triazol-1-yl)-1-(2,3-dideoxy-4-cyano-5'-O-acetyl-$\beta$-D-erythropentofuranosyl) pyrimidin-2(1H)-one (60 mg, 0.18 mM) was treated with aqueous ammonia (1 ml) and methanol (1 ml) at room temperature for 3 hours. The solvent was evaporated and the residue was chromatographed on silica gel (Preparative TLC) eluting with 12% CH3OH/CH2Cl2 to give 2',3'-dideoxy-4'-cyano cytidine (14 mg, 0.06 mM). Accurate Mass Calcd. for $C_{10}H_{12}N_4O_3$: 236.0909. Found: 236.0909.

EXAMPLE 8

4-azidomethylthymidin-2'-ene

A. Formula I Where B is Thymine, Z' is $CH_2N_3$

To a solution of the 4'-$\alpha$ and 4'-$\beta$ isomers of 2'-deoxy-4'-methanesulfonyloxymethylthymidin-2'ene (170 mg, 0.5 mM), prepared, e.g., as described in Preparation 24, in HMPA (hexamethylphosphoramide) (3 ml), add LiN3 (250 mg, 5 mM) and stir at 90° C. for 18 hours. To purify, add ether and hexane with vigorous stirring at 24° C. and allow solution to clear. After decanting the ether/hexane solution (containing most of the HMPA), the remaining oily residue is purified by flash chromatography (silica gel on a short column) eluting with acetone/EtOAc (1:1). The eluant was concentrated by removal of the solvents by evaporation and the residue was trice flash chromatographed on silica gel (medium column, 12 inches) eluting with CH2Cl2+5% MeOH. The eluant was concentrated by removal of the solvents by evaporation under pump vacuum to yield the 4'-$\alpha$ and 4'-$\beta$ isomers of 4-azidomethylthymidin-2'-ene, 55 mg (mp 118°–119° C.) and 47 mg (mp 122°–123° C.), respectively B. Formula I Varying B By following the procedure of part A and substituting for the 4'-$\alpha$ and 4'-$\beta$ isomers of 2'-deoxy-4'- methanesulfonyloxymethylthymidin-2'-ene the the 4'-α and 4'-β isomers of following:

2',3'-dideoxy-4'-methanesulfonyloxymethyladenosin-2'-ene,
2',3'-dideoxy-4'-methanesulfonyloxymethylguanosin-2'-ene,
2',3'-dideoxy-4'-methanesulfonyloxymethyluridin-2'-ene,
2',3'-dideoxy-4'-methanesulfonyloxymethylcytidin-2'-ene,
9-(2,3-dideoxy-4-methanesulfonyloxymethyl-β-D-erythro-pento-2-furenyl)-2,6-diaminopurine, and
9-(2,3-dideoxy-4-methanesulfonyloxymethyl-β-D-erythro-pento-2-furenyl)-6-oxopurine;

there are obtained the 4'-α and 4'-β isomers of the following respective compounds:

2',3'-dideoxy-4'-azidomethyladenosin-2'-ene,
2',3'-dideoxy-4'-azidomethylguanosin-2'-ene,
2',3'-dideoxy-4'-azidomethyluridin-2'-ene,
2',3'-dideoxy-4'-azidomethylcytidin-2'-ene,
9-(2,3-dideoxy-4-azidomethyl-β-D-erythropento-2-furenyl)-2,6-diaminopurine, and
9-(2,3-dideoxy-4-azidomethyl-β-D-erythropento-2-furenyl)-6-oxopurine.

EXAMPLE 9

1-(1-β-hvdroxymethyl-2.6-dioxabicyclo[3.2.0]hept-3β-yl)thymine

A. Formula I-H Where Y' is O and Z' is —CH$_2$— such that Y' and Z' together is —O—CH$_2$—

A mixture of N$^3$-benzoyl-4'-hydroxymethyl thymidine, prepared, for example, as described in preparation 27 (0.24 g, 0.67 mM), triphenylphosphine (0.28 g, 1.07 mM) and diethylazodicarboxylate (0.16 ml, 1 mM) in THF (5 ml) was heated at 60° C. for 16 hours. The solvent was evaporated and the residue was chromatographed on silica gel with 2.5% CH$_3$OH/CH$_2$Cl$_2$ to give N$^3$-benzoyl-1-(1-β-hydroxymethyl-2,6-dioxabicyclo[3.2.0]hept-3β-yl)thymine (0.06 g, 0.17 mM). The above compound (60 mg) was then treated with NH$_4$OH/CH$_3$OH (1:1) (0.5 ml) at 24° C. for 3 hours. After evaporation of the solvent and chromatography on silica gel using 6% CH$_3$OH/CH$_2$Cl$_2$ as eluent. 1-(1-β-hydroxymethyl-2,6-dioxabicyclo[3.2.0]hept-3β-yl)thymine (0.015 g, 0.06 mM) was obtained.

B. Formula I Varying B

By following the procedure of part A and substituting for N$^3$-benzoyl-4'-hydroxymethyl thymidine the following:

N$^6$-benzoyl-2'-deoxy-4'-hydroxymethyl adenosine,
N$^1$,N$^2$-dibenzoyl-2'-deoxy-4'-hydroxymethyl guanosine,
N$^3$-benzoyl-2'-deoxy-4'-hydroxymethyl uridine,
N$^4$-benzoyl-2'-deoxy-4'-hydroxymethyl cytosine,
N$^2$,N$^6$-dibenzoyl-9-(2-deoxy-4-hydroxymethyl-β-D-erythro-pentofuranosyl)-2,6-diaminopurine, and
N$^1$-benzoyl-9-(2-deoxy-4-hydroxymethyl-β-D-erythro-pentofuranosyl)-6-oxopurine;

there are obtained the following compounds:

9-(1-β-hydroxymethyl-2,6-dioxabicyclo[3.2.0]hept-3β-yl)adenine,
9-(1-β-hydroxymethyl-2,6-dioxabicyclo[3.2.0]hept-3β-yl)guanine,
1-(1-β-hydroxymethyl-2,6-dioxabicyclo[3.2.0]hept-3β-yl)uracil,
1-(1-β-hydroxymethyl-2,6-dioxabicyclo[3.2.0]-hept-3β-yl)cytosine,
9-(-β-D-erythro-pentofuranosyl)-2,6-diaminopurine and 9-hydroxymethyl-2,6-dioxabicyclo[3.2.0]hept-3β-yl)-2,6-diaminopurine, and
9-(2-deoxy-4-azidomethyl-β-D-erythro-pentofuranosyl)-6-oxopurine and
9-(1-β-hydroxymethyl-2,6-dioxabicyclo[3 2 0]hept-3β-yl)-6-oxopurine.

EXAMPLE 10

This example illustrates the preparation of a representative pharmaceutical formulation for oral administration containing an active compound of Formula I, e.g., 1-(1-β-hydroxymethyl-2,6-dioxabicyclo[3.2.0]hept-3β-yl)thymine.

| Ingredients | Quantity per tablet, mgs. |
|---|---|
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1-9, such as 4'-azidomethylthymidine, can be used as the active compound in the preparation of the orally administrable formulations of this example.

EXAMPLE 11

This example illustrates the preparation of a representative pharmaceutical formulation containing an active compound of Formula I, e.g., 1-(1-β-hydroxymethyl-2,6-dioxabicyclo[3.2.0]hept-3β-yl)thymine.

A suspension for oral administration is prepared having the following composition:

| Ingredients | Quantity |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1-9, such as 4'-azidomethylthymidine, can be used as the active compound in the preparation of the orally administrable formulations of this example.

EXAMPLE 12

This example illustrates the preparation of a representative pharmaceutical formulation containing an active compound of Formula I, e.g., 1-(1-β-hydroxymethyl-2,6-dioxabicyclo[3.2.0]hept-3β-yl)thymine.

An injectable preparation is prepared having the following composition:

| Ingredients | |
|---|---|
| Active compound | 0.2 g |
| water (distilled, sterile) | q.s. to 20.0 mL |

Other compounds of Formula I, such as those prepared in accordance with Examples 1,2 and 4–9, such as 4'-azidomethylthymidine, can be used as the active compound in the preparation of the injectable formulations of this example.

Compounds of Formula I having low solubility in water can be formulated for intravenous injection in liposomes.

EXAMPLE 13

This example illustrates the preparation of a representative pharmaceutical formulation for topical application containing an active compound of Formula I, e.g., 1-(1-β-hydroxymethyl-2,6-dioxabicyclo[3.2.0]hept-3β-yl)thymine.

| Ingredients | grams |
|---|---|
| Active compound | 0.2–10 |
| Span 60 | 2.0 |
| Tween 60 | 2.0 |
| Mineral oil | 5.0 |
| Petrolatum | 10.0 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added, q.s. to 100 g.

Other compounds of Formula I, such as those prepared in accordance with Examples 1,2 and 4–9, such as 4'-azidomethylthymidine can be used as the active compound in the preparation of the topical formulations of this example.

EXAMPLE 14

This example illustrates the preparation of a representative pharmaceutical formulation containing an active compound of Formula I, e.g., 1-(1-β-hydroxymethyl-2,6-dioxabicyclo[3.2.0]hept-3β-yl)thymine.

A suppository totalling 2.5 grams is prepared having the following composition:

Active compound 500 mg
witepsol H-15* balance
(*triglycerides of saturated vegetable fatty acid; a product of Riches-Nelson, Inc., New York, N.Y.).

Other compounds of Formula I, such as those prepared in accordance with Examples 1,2 and 4–9, such as 4'-azidomethylthymidine can be used as the active compound in the preparation of the suppository formulations of this example.

EXAMPLE 15

This example illustrates the preparation of another representative pharmaceutical formulation for oral administration, containing an active compound of Formula I, e.g., 1-(1-β-hydroxymethyl-2,6-dioxabioyclo[3.2.0]hept-3β-yl)thymine.

| Ingredients | Quantity per tablet, mgs. |
|---|---|
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 1,2 and 4–9, such as 4'-azidomethylthymidine can be used as the active compound in the preparation of the orally administrable formulations of this example.

EXAMPLE 16

Liposome Formulation With 4'-Azidomethylthymidine 5'-monophosohate

Sufficient water is added to 100 g of egg-yolk phospholipids to bring the total volume to 1 liter. The mixture is stirred with a homomixer. Then, the mixture is homogenized with an emulsifier under a pressure of 300 kg/cm$^2$ for 30 minutes, whereby an aqueous phospholipid dispersion is obtained 4'-Azidomethylthymidine 5'-monophosphate (20 g) and sodium chloride (18 g) are dissolved in enough water to bring the total volume to 1 liter. The aqueous phospholipid dispersion (850 mL) and the 4'-azidomethylthymidine 5'-monophosphate solution (850 mL) are mixed. The aqueous dispersion thus obtained is filtered through a membrane filter (pore size 0.45 m in diameter). The filtrate is sterilized at 120° C. for 20 minutes and then allowed to stand at −20° C. for 20 hours in a freezer. The frozen dispersion thus obtained is thawed by allowing it to stand at room temperature. An aqueous suspension of 4'-azidomethylthymidine 5'-monophosphate entrapped in phospholipid spherules is thereby obtained.

Other compounds of Formula I, such as those prepared in accordance with Examples 1,2 and 4–9, particularly the phosphate esters, can be used as the active compound in the preparation of formulation according to this example.

EXAMPLE 17

Liposome Formulation With 2'-deoxy-4'-Cyanouridine 2',3'-dipalmitoate

Phosphatidylcholine (30 mM), cholesterol (15 mM) and cholesterol sulfate (5 mM) are dissolved in a 2:1 mixture of chloroform:methanol To this, 2'-deoxy-4'-cyanouridine 3',5'-dipalmitoate (5 mM) is added and the mixture is stirred in a round bottom flask The solvents are removed by evaporation under reduced pressure to form a film on the inner surface of the flask The film is dried in vacuo. Saline (2.5 mL) is added and the solution is shaken under N$_2$ to swell the film and prepare a lipid suspension The suspension is sonicated at 10°–17° C. for 50 minutes at 20 KHz and 35 W by a probe-type sonicator under N$_2$. The size of the liposomes obtained range from 22–55 mm in diameter.

Other compounds of Formula I, such as the 3',5'-diadamantoate, preferably the long chain acyl derivatives of Formula I, can be used as the active compound in the preparation of liposomal formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of spirit and scope of the present invention. All such modifications are intended to be within the scope of the claims appended hereto.

What is claimed is:

1. A compound of the formula

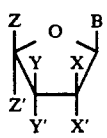

I wherein:
B is a purine or a pyrimidine;
X and X' are H;
Y is H;
Y, is OH or H; or Y' and X' together makes a bond;
Z is

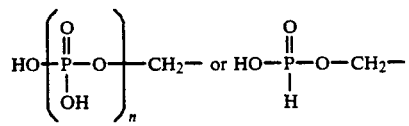

where n is zero, one, two or three;
or Y' and Z together form a cyclic phosphate ester;
Z' is —CN, —CH$_3$, —CH$_2$N$_3$ or —CH$_2$J, where J is a halogen atom;
or Z' and Y' together are —CH$_2$O—;
and pharmaceutically acceptable esters, ethers, amides, N-acyl moieties and salts thereof.

2. The compound of claim 1, where B is selected from the group consisting of:
adenine, guanine, uracil, thymine, cytosine, hypoxanthine, 2,6-diaminopurine, 2-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-fluoro-2,4-dioxopyrimidine, 5-chloro-2,4-dioxopyrimidine, 5-bromo-2,4-dioxopyrimidine, 5-iodo-2,4-dioxopyrimidine, and 5-trifluoromethyl-2,4-dioxopyrimidine.

3. The compound of claim 2 where Z' and Y' together are —CH$_2$O—.

4. The compound of claim 3 where B is a pyrimidine.

5. The compound of claim 4 where Z is

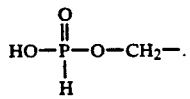

6. The compound of claim 4 where X, X' and Y are H, and Z is in which n is zero.

7. The compound of claim 6

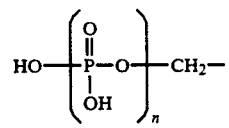

where B is thymine, namely 1-(1-β-hydroxymethyl-2,6-dioxabicyclo[3.2.0]hept-3β-yl)thymine.

8. The compound of claim 6 where B is cytosine, namely 1-(1-β-hydroxymethyl-2,6-dioxabicyclo[3.2.0]hept-3β-yl)cytosine.

9. The compound of claim 2 where Z' is —CN, —CH$_3$, —CH$_2$N$_3$ or —CH$_2$J, where J is a halogen atom.

10. The compound of claim 9 where Z is

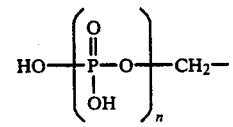

in which n is zero.

11. The compound of claim 10 where X, X' and Y are H, and Y' is OH.

12. The compound of claim 11 where Z' is —CN and B is thymine, namely 4'-cyanothymidine.

13. The compound of claim 11, where Z' is —CH$_3$ and B is thymine, namely 4'-methylthymidine.

14. The compound of claim 11, where Z' is —CN and B is cystosine, namely 2'-deoxy-4'-cyanocytidine.

15. The compound of claim 11, where Z' is —CH$_2$N$_3$ and B is thymine, namely 4'-azidomethylthymidine.

16. The compound of claim 11, where Z' is —CH$_2$J.

17. The compound of claim 11, where Z' is —CN and B is uracil, namely 2'-deoxy-4'-cyanouridine.

18. The compound of claim 11, where Y' is H.

19. The compound of claim 17, where Z' is —CN and B is cytosine, namely 2',3'-dideoxy-4'-cyanocytidine.

20. The compound of claim 10 where Y' and X' together makes a bond.

21. The compound of claim 20, where Z' is —CH$_2$N$_3$ and B is thymine, namely 4'-azidomethylthymidin-2'-ene.

22. A pharmaceutical composition comprising a pharmaceutically acceptable non-toxic excipient and a therapeutically effective amount of a compound of claim 1.

23. The pharmaceutical composition of claim 22 further comprising a therapeutically effective amount of a second antiviral agent.

24. The pharmaceutical composition of claim 23 where said second antiviral agent is acyclovir, ganciclovir or foscarnet.

25. The pharmaceutical composition of claim 24, wherein the compound of Formula I is 1-(1-β-hydroxymethyl-2,6-dioxabicyclo[3.2.0]hept-3β-yl)thymine.

26. The pharmaceutical composition of claim 24, wherein the compound of Formula I is 4'-cyanothymidine.

27. The pharmaceutical composition of claim 24, wherein the compound of Formula I is 4'-azidomethylthymidine.

28. The pharmaceutical composition of claim 24, wherein the compound of Formula I is 4'-methylthymidine.

29. The pharmaceutical composition of claim 24, wherein the compound of Formula I is 2',3'-dideoxy-4'-cyanocytidine.

30. A process for making a compound of the formula:

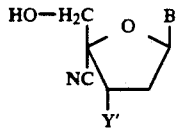

wherein:
B is a purine or a pyrimidine; and
Y' is H or OH; said process comprising:
contacting aqueous ammonia with a compound of the formula:

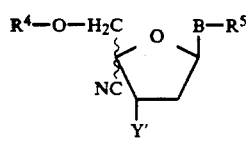

wherein:
B is a purine or a pyrimidine;
Y' is H or —O—$R^4$, where $R^4$ is an acyl group; and
$R^5$ is 1,2,4-triazole.

31. A process for making a compound of the formula:

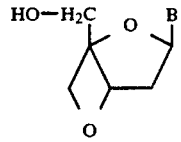

wherein:
B is a purine or a pyrimidine; said process comprising:
contacting a dehydration reagent mixture with a compound of the formula:

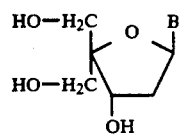

wherein:
B is a purine or a pyrimidine; and
$R^6$ is an acyl group.

* * * * *